(12) United States Patent
Phillips

(10) Patent No.: US 7,520,890 B2
(45) Date of Patent: Apr. 21, 2009

(54) REINFORCED GRAFT AND METHOD OF DEPLOYMENT

(76) Inventor: Peter W. Phillips, Lombard Medical Technologies plc, 4 Trident Park, Didcot, Oxfordshire OX11 7HJ (GB)

( * ) Notice: Subject to any disclaimer, the term of this patent is extended or adjusted under 35 U.S.C. 154(b) by 278 days.

(21) Appl. No.: 11/051,614

(22) Filed: Feb. 4, 2005

(65) Prior Publication Data

US 2005/0143806 A1    Jun. 30, 2005

Related U.S. Application Data

(63) Continuation-in-part of application No. 09/601,023, filed as application No. PCT/GB99/00261 on Jan. 26, 1999, now Pat. No. 6,899,728.

(30) Foreign Application Priority Data

Jan. 26, 1998  (GB) ................................. 9801660.3
Jan. 31, 1998  (GB) ................................. 9802060.5

(51) Int. Cl.
    *A61F 2/06* (2006.01)
(52) U.S. Cl. ..................... 623/1.13; 623/1.35
(58) Field of Classification Search ............... 623/1.11, 623/1.13, 1.35, 903; 606/191–195
    See application file for complete search history.

(56) References Cited

U.S. PATENT DOCUMENTS

| | | |
|---|---|---|
| 3,527,223 A | 9/1970 | Shen |
| 3,716,058 A | 2/1973 | Tanner |
| 4,241,681 A | 12/1980 | Porter |
| 4,275,813 A | 6/1981 | Noiles |
| 4,317,451 A | 3/1982 | Cerwin et al. |
| 4,352,542 A | 10/1982 | Tydings |
| 4,485,816 A | 12/1984 | Krumme |
| 4,502,159 A | 3/1985 | Woodroof et al. |
| 4,503,569 A | 3/1985 | Dotter |
| 4,512,338 A | 4/1985 | Balko et al. |
| 4,590,938 A | 5/1986 | Segura et al. |
| 4,800,882 A | 1/1989 | Gianturco |
| 4,907,336 A | 3/1990 | Gianturco |
| 4,921,484 A | 5/1990 | Hillstead |
| 5,015,253 A | 5/1991 | MacGregor |
| 5,041,126 A | 8/1991 | Gianturco |
| 5,042,707 A | 8/1991 | Taheri |
| 5,161,547 A | 11/1992 | Tower |
| 5,192,291 A | 3/1993 | Pannek |
| 5,192,301 A | 3/1993 | Kamiya et al. |
| 5,219,358 A | 6/1993 | Bendel et al. |
| 5,222,971 A | 6/1993 | Willard |
| 5,226,913 A | 7/1993 | Pinchuk |

(Continued)

FOREIGN PATENT DOCUMENTS

DE    19711288 A    10/1998

(Continued)

*Primary Examiner*—Alvin J. Stewart
(74) *Attorney, Agent, or Firm*—Craig A. Fieschko, Esq.; DeWitt Ross & Stevens S.C.

(57) ABSTRACT

A graft is provided with a flexible sheet (10) of graft material to which is sewn a reinforcing wire (12), preferably of shape-memory alloy. Sewing of the wire (12) is carried out while the sheet (10) is substantially planar, thus by conventional embroidery machines. The sheet (10) is subsequently rolled into a tubular shape.

20 Claims, 31 Drawing Sheets

U.S. PATENT DOCUMENTS

| | | | |
|---|---|---|---|
| 5,263,973 A | 11/1993 | Cook | |
| 5,282,824 A | 2/1994 | Gianturco | |
| 5,314,444 A | 5/1994 | Gianturco | |
| 5,330,490 A | 7/1994 | Wilk | |
| 5,389,106 A | 2/1995 | Tower | |
| 5,403,341 A | 4/1995 | Solar | |
| 5,413,584 A | 5/1995 | Schulze | |
| 5,433,723 A | 7/1995 | Lindenberg et al. | |
| 5,445,646 A | 8/1995 | Euteneuer et al. | |
| 5,507,771 A | 4/1996 | Ginaturco | |
| 5,527,338 A | 6/1996 | Purdy | |
| 5,531,760 A | 7/1996 | Alwafaie | |
| 5,540,716 A | 7/1996 | Hlavacek | |
| 5,562,697 A | 10/1996 | Christiansen | |
| 5,571,135 A | 11/1996 | Fraser et al. | |
| 5,573,543 A | 11/1996 | Astashov et al. | |
| 5,575,816 A | 11/1996 | Rudnick et al. | |
| 5,578,071 A * | 11/1996 | Parodi | 623/1.19 |
| 5,586,983 A | 12/1996 | Sanders et al. | |
| 5,591,230 A | 1/1997 | Horn et al. | |
| 5,601,593 A | 2/1997 | Freitag | |
| 5,618,311 A | 4/1997 | Gryskiewicz | |
| 5,632,746 A | 5/1997 | Pyka et al. | |
| 5,707,376 A | 1/1998 | Kavteladze et al. | |
| 5,718,724 A | 2/1998 | Goicoechea et al. | |
| 5,720,755 A | 2/1998 | Dakov | |
| 5,723,004 A * | 3/1998 | Dereume et al. | 623/1.35 |
| 5,733,325 A | 3/1998 | Robinson et al. | |
| 5,746,766 A | 5/1998 | Edoga | |
| 5,782,904 A | 7/1998 | White et al. | |
| 5,800,515 A | 9/1998 | Nadal et al. | |
| 5,814,063 A | 9/1998 | Freitag | |
| 5,824,037 A | 10/1998 | Freislinger et al. | |
| 5,824,040 A | 10/1998 | Freislinger et al. | |
| 5,843,117 A | 12/1998 | Alt et al. | |
| 5,843,158 A | 12/1998 | Lenker et al. | |
| 5,873,906 A | 2/1999 | Lau et al. | |
| 5,876,432 A | 3/1999 | Lau et al. | |
| 5,891,193 A | 4/1999 | Robinson et al. | |
| 5,919,225 A | 7/1999 | Lau et al. | |
| 5,935,161 A | 8/1999 | Robinson et al. | |
| 5,941,890 A | 8/1999 | Boehm et al. | |
| 5,980,565 A | 11/1999 | Jayaraman | |
| 5,984,949 A | 11/1999 | Levin | |
| 5,990,378 A | 11/1999 | Ellis | |
| 6,001,123 A | 12/1999 | Lau | |
| 6,015,429 A | 1/2000 | Lau et al. | |
| 6,017,362 A | 1/2000 | Lau | |
| 6,024,763 A | 2/2000 | Lenker et al. | |
| 6,042,605 A | 3/2000 | Martin et al. | |
| 6,071,292 A | 6/2000 | Makower et al. | |
| 6,093,205 A | 7/2000 | McLeod et al. | |
| 6,110,198 A | 8/2000 | Fogarty et al. | |
| 6,113,611 A | 9/2000 | Allen et al. | |
| 6,123,722 A | 9/2000 | Fogarty et al. | |
| 6,176,875 B1 | 1/2001 | Lenker et al. | |
| 6,190,401 B1 | 2/2001 | Green et al. | |
| 6,193,745 B1 | 2/2001 | Fogarty et al. | |
| 6,200,330 B1 | 3/2001 | Benderev et al. | |
| 6,200,336 B1 | 3/2001 | Pavcnik et al. | |
| 6,210,429 B1 * | 4/2001 | Vardi et al. | 623/1.11 |
| 6,273,903 B1 | 8/2001 | Wilk | |
| 6,283,991 B1 | 9/2001 | Cox et al. | |
| 6,287,315 B1 | 9/2001 | Wijeratne et al. | |
| 6,309,415 B1 | 10/2001 | Pulnev et al. | |
| 6,334,867 B1 | 1/2002 | Anson | |
| 6,419,686 B1 | 7/2002 | McLeod et al. | |
| 6,432,134 B1 | 8/2002 | Anson et al. | |
| 6,447,524 B1 | 9/2002 | Knodel et al. | |
| 6,451,034 B1 | 9/2002 | Gifford et al. | |
| 6,475,232 B1 | 11/2002 | Babbs et al. | |
| 6,485,496 B1 | 11/2002 | Suyker et al. | |
| 6,508,833 B2 | 1/2003 | Pavcnik et al. | |
| 6,565,596 B1 | 5/2003 | White et al. | |
| 6,565,597 B1 | 5/2003 | Fearnot et al. | |
| 6,576,009 B2 | 6/2003 | Ryan et al. | |
| 6,582,458 B1 | 6/2003 | White et al. | |
| 6,592,614 B2 | 7/2003 | Lenker et al. | |
| 6,613,073 B1 | 9/2003 | White et al. | |
| 6,685,736 B1 | 2/2004 | White et al. | |
| 6,689,158 B1 | 2/2004 | White et al. | |
| 6,814,747 B2 | 11/2004 | Anson et al. | |
| 6,843,803 B2 | 1/2005 | Ryan et al. | |
| 2002/0099437 A1 | 7/2002 | Mazzocchi | |
| 2002/0120327 A1 | 8/2002 | Cox et al. | |
| 2002/0138095 A1 | 9/2002 | Mazzocchi et al. | |
| 2002/0177890 A1 | 11/2002 | Lenker | |
| 2003/0125795 A1 | 7/2003 | Pavcnik et al. | |
| 2004/0122508 A1 | 6/2004 | White et al. | |

FOREIGN PATENT DOCUMENTS

| | | |
|---|---|---|
| EP | 0508473 A2 | 10/1992 |
| EP | 0759287 A1 | 8/1995 |
| FR | 2725126 A | 4/1996 |
| FR | 2746292 | 9/1997 |
| WO | 98/07385 | 2/1998 |
| WO | 98/52496 A | 11/1998 |
| WO | 00/07506 A2 | 2/2000 |
| WO | 01/30269 A1 | 5/2001 |

* cited by examiner

REINFORCED GRAFT AND METHOD OF DEPLOYMENT

CROSS-REFERENCE TO RELATED APPLICATIONS

This application is a continuation-in-part under 35 USC §120 of U.S. patent application Ser. No. 09/601,023 filed 26 Jul. 2000 (now U.S. Pat. No. 6,899,728), which in turn claims the priority under 35 USC §371 of International (PCT) Patent application PCT/GB99/00261 filed 26 Jan. 1999, which in turn claims priority to GB 9802060.5 filed 31 Jan. 1998 and GB 9801660.3 filed 26 Jan. 1998. In addition, this application claims the benefit under 35 USC §119 of GB 0402499.8 filed 4 Feb. 2004. All of these prior applications are incorporated by reference herein.

FIELD OF THE INVENTION

This invention relates to a reinforced graft and to a method of producing such a graft which may be used for the treatment of lesions in vessels, e.g., aneurysms in the aorta or lesions in the esophagus or trachea, by an endoluminal technique, which is minimally invasive and which can therefore be used on many patients who are too old or frail to be able to withstand conventional surgery.

BACKGROUND OF THE INVENTION

Conventional vascular grafts commonly consist of a textile or polymer tube which is implanted into a patient in a major open surgical procedure. grafts which have been implanted endoluminally, that is from within the vessel, consist of grafts which are combined with stents. Such grafts are very time-consuming to produce and this causes particular problems when a bespoke graft is required to be produced at short notice.

Additionally, one of the major problems of existing vascular grafts for endoluminal surgery is that, because of the tortuous bends commonly encountered between the aorta and iliac arteries of patients with aneurysms, there is a tendency for existing tubular grafts to collapse at least partially. This is because, when the tube is curved for any reason, the external diameter of the curve is necessarily longer than the internal, and the excess graft material on the internal diameter of the curve kinks into the lumen, thereby narrowing or even closing it completely. This problem also arises in vascular grafts for repair of, for example, the popliteal artery because of the extreme bending movements which are imparted to this artery during knee flexion.

Furthermore once a graft has been introduced into an artery by the surgeon and located at the correct position, it is necessary to ensure that it is reliably held at such position.

Some devices in use to date are based upon the combination of a stent with a graft, a stent being a relatively rigid metallic cylinder with highly fenestrated walls. This produces a strong implant but one which is relatively inflexible. Some prior graft stents comprise a woven fabric tube which is supported by a series of wire rings which are stitched to the outer or inner surfaces of the implant. Usually these rings are made in the form of a 'Z' stent (as with the ZENITH graft manufactured by Cook Inc., or the TALENT graft manufactured by Medtronic Inc.). The 'Z' stent, as well as other graft stents, is known to be relatively inflexible and for this reason, graft stents manufactured using such supports are not easily bent around curved vessels. (A frequent complication of arterial disease is the development of highly tortuous vessels through which it is very difficult to pass substantially rigid graft stents.) Moreover the graft stents are difficult to compress axially and this requires that the length of the patient's vessels must be measured accurately so that the selected graft stent is a good fit. Estimating the length of graft stent required to fit a patient can be surprisingly difficult because the presence of the graft stent itself modifies the anatomy of the patient, straightening tortuous vessels and taking unpredictable paths through aneurysmal voids.

Once measured, another problem for the practitioner is to place the graft stent in the same position as was planned; generally the top or proximal end of the implant is deployed first and the rest of the implant follows. If the top is incorrectly placed, then it follows that the bottom of the implant will also be incorrectly placed because the implants cannot be significantly compressed along their axes.

Most graft stents require the inflation of a balloon inside them to expand the graft to fit within the blood vessel although self expanding designs have been recently introduced.

Most existing designs involve the use of a preformed stent which usually involves expensive construction techniques such as laser cutting and plasma welding.

In attaching the preformed stent to the graft, current devices usually involve multiple individual stitches around the stent and attached to the graft. These stitches are necessarily attached by hand in a costly and time consuming process.

A further problem with the current designs, arising from the substantial stent components, is the difficulty in designing bifurcated grafts which can be used at, for instance, the aorto-iliac bifurcation.

A further problem associated with long graft stents, particularly in the arteries of the lower limb, is irritation of the arteries arising from trauma of insertion and the longer term presence of the synthetic material.

SUMMARY OF THE INVENTION

The present invention seeks to provide an improved reinforced graft and method of making such a graft.

According to an aspect of the present invention, there is provided a graft including a sheet of flexible material, a plurality of reinforcement elements extending transversely relative to a longitudinal direction of the sheet of material, the reinforcement elements being spaced from one another in the longitudinal direction, wherein at least some of the plurality of reinforcement elements are formed from a continuous wire.

Advantageously, the sheet of material is formed as a tube with the reinforcement elements extending annularly around the tube.

The reinforcement elements are preferably compressible radially relative to the tube.

When the graft is formed into its in-use shape, the reinforcing elements are preferably pre-stressed. This enables the use of reinforcement elements which are more deformable than prior art devices.

According to another aspect of the present invention, there is provided a graft including at least one radio-opaque marker embroidered onto the graft. Advantageously, the marker provides an indication of the part of the graft to which the marker is embroidered. For example, the marker could denote an "L", "R", "A" or "P" denoting, respectively, left, right, anterior and posterior. A plurality of opaque markers could be provided on the graft.

It will be apparent that an embroidered marker could also be provided on a stent by providing embroiderable material on the stent.

According to another aspect of the present invention there is provided a graft or stent including at one extremity thereof a plurality of flexible members extending in a longitudinal direction of the graft or stent from an annular perimeter thereof, an annulus being provided at a free extremity of the flexible members, the flexible members being deformable substantially to a point to provide a flexible neck about which the annulus can rotate. This structure can provide a front guide to the graft or stent considerably facilitating insertion of the graft or stent into, for example, an artery, and greatly improving fixation in highly tortuous vessels.

Preferably, the elongate members provide a flow path into the graft or stent.

In the preferred embodiment, the elongate members are provided with barbs at their extremities remote from the graft or stent, for fixing the graft or stent into, for example, an artery.

Alternatively, separate barbs may be provided on the annulus.

According to another aspect of the present invention, there is provided a method of forming a reinforced graft, including providing a sheet of material, a plurality of reinforcement elements in substantially flat configuration, sewing the reinforced elements to the fabric, forming the fabric into a substantially tubular shape.

This method enables the graft to be produced by conventional sewing machines.

Preferably, the method includes a step of sewing guides over the reinforcement elements, moving the reinforcement elements into their correct position on the sheet of material, and then sewing the reinforcement elements into substantially fixed positions on the sheet of material.

Advantageously, the reinforcement elements are sewn loosely onto the sheet of material. For example, spaced stitches could be used to enable slight buckling of the material between stitches during compression of the graft. Alternatively, stitches which have a stitch width of 2 to 9 times the width of the reinforcement elements could be used.

Advantageously, a reduced friction coated yarn is used to enable some movement of the reinforcement elements relative to the sheet of material, particularly on compression of the finished graft.

In the preferred embodiment, the reinforcement elements are provided by a single wire sewn into a ladder of substantially straight portions connected by substantially U-shaped connecting portions. The connecting portions may be round or substantially square in shape.

Advantageously, the graft is formed so that connecting portions overlap. In the preferred embodiment overlapping connection portions are sewn to one another.

According to another aspect of the present invention, there is a provided a method of forming a reinforced graft or stent in which reinforcement elements are connected to a flexible fabric sheet by means of a lock-stitch or chain-link.

According to another aspect of the present invention, there is provided a reinforced graft including a sheet of flexible material and a plurality of reinforcement elements, the reinforcement elements being substantially parallel to the weft or warp of the fabric or substantially at 450 to the weft or warp of the fabric. Providing reinforcement elements substantially parallel to the weft or warp of the fabric to provide a stable and substantially inelastic structure. On the other hand, providing reinforcement elements at substantially 450 to the weft or warp provides a more elastic device.

The preferred embodiment can provide a reinforced graft which is sufficiently flexible to allow it to be drawn through tortuous vessels and which has sufficient radial stiffness to resist kinking and subsequent collapse which would occlude the flow of blood through the graft. It can be used for endovascular implantation in diseased arteries such as the aorta, carotid, iliac, femoral and popliteal arteries. Other applications of the device exist in vessels in the body such as veins, bile ducts, oesophagus, trachea etc.

Preferably, the reinforced graft is self expanding to the extent that it does not require a balloon for inflation.

Advantageously, the reinforced graft does not involve the separate manufacture and attachment of a stent and can be manufactured simply and relatively quickly. The simplicity of the preferred construction is intended to assist in the production of bifurcated, tapered and connecting grafts.

It is preferred that the graft is sufficiently supple that it can be everted so that when initially inserted, the proximal part of the graft can be held and the distant part pulled through the proximal part so that finally, the graft is everted end to end. This possibility reduces the trauma of implanting long lengths of graft.

An example of a method of producing a reinforced graft comprises the steps of attaching filamentary reinforcing material to a sheet of flexible graft material having opposite side edges so that the reinforcing material extends laterally over the sheet with respect to the opposite side edges and is preferably attached along substantially the whole of its length to the sheet; forming the sheet into a tube having a longitudinal seam; and preferably securing together the reinforcing material on opposite sides of the longitudinal seam.

In this example, the reinforcing material can be very accurately and conveniently attached at the required places to the sheet when the latter is laid out flat and before the sheet is formed into a tube, thus avoiding the complication of attaching the reinforcing material to a pre-formed tube of graft material.

Preferably, the filamentary reinforcing material is attached to the sheet of flexible graft material so as to define a sinuous pattern of the reinforcing material in which a multiplicity of substantially linear regions extending laterally with respect to the sheet are joined by bends, and the bends at one side of the sinuous pattern are secured to corresponding regions of the reinforcing material at the other side. In this way, spaced hoops of filamentary reinforcing material are provided which are secured to the tube, the hoops being spaced apart in the longitudinal direction of extent of the tube. It will be understood that these hoops can be appropriately spaced apart so as to permit the required flexibility of the tube to enable it to be bent around tortuous bends commonly encountered in the arteries of patients whilst still supporting the tube in such a way as to prevent kinking thereof exclusively in a localized region. Thus, when the tube is bent, it is constrained to bend in a series of small kinks between the reinforcing hoops, and thereby able to follow curvatures encountered in practice without significant stenosis of the lumen.

In a particularly preferred embodiment, the bends are secured using ties which are not passed through the wall of the tube.

This may be effected simply by passing the ties solely around the part of the filamentary material to be joined together and knotting them.

The seam in the tube is preferably formed by securing the sheet along the side edges and then folding the portion of the tube in the region of the seam so that the fold is disposed on the outside of the tube.

Another example of a method of producing a reinforced graft comprises the steps of securing filamentary anchor material to flexible graft material by attaching it to the graft material over a plurality of spaced bends in the filamentary anchor material; and cutting the filamentary material at regions between the bends so as to form a multiplicity of bristles or barbs of the filamentary material which project from the flexible graft material.

The bristles or barbs (hereinafter generally referred to simply as bristles) act as effective anchors which retain the graft in place in use and may even be longer than the thickness of the wall of the artery or other organ into which the graft is to be fitted.

Preferably, the flexible graft material is in the form of a sheet, and this method includes the step of forming the sheet into a tube so that the filamentary anchor material is disposed on the outer surface of the tube. The cutting step may be performed before the tube is formed but is preferably performed after.

Preferably, the bends are formed so that, although they may all face in the same general direction relative to the direction of extent of the tube, some of the bristles extend from the bends at different angles relative to others in the direction of extent of the tube. This may be achieved by making some of the bends tighter than others.

The sheet of flexible graft material may be a woven or nonwoven fabric formed e.g. of a suitable bio-compatible polymer such as a bio-compatible polyester. A woven polyester microfibre (typically, 6-7 Fm diameter fibre) fabric is particularly preferred, which may be coated for example with gelatine or other material to enhance tissue in-growth or reduce thrombogenicity or permeability.

The filamentary material may be attached to one surface of the sheet by gluing or welding. However, it is preferred to effect the attachment by stitching, preferably using a computer controlled embroidery machine. Stitching may be effected over substantially the whole of the length of the filamentary reinforcing material which is fully secured to the sheet of flexible graft material and thus incapable of being displaced relative to the sheet.

The filamentary material is preferably a material having superelastic and/or shape-memory properties, e.g. a superelastic, shape-memory alloy such as a nickel-titanium alloy (e.g. Nitinol –50 Ni/50 Ti), and is preferably also in the form of a wire. The wire may have a diameter of about 0.2 mm. However, it is within the scope of the present invention for the reinforcing material to be any suitable bio-compatible material suitable for implantation, for example nylon, polyester, silk, polyglycolic acid, polyactic acid, metal or alloy or any combination thereof.

The preferred embodiment includes a combination of the features and methods described herein. Thus, it is preferred for portions of the filamentary reinforcing material used in the first method described above to define the plurality of bends provided in the second method described above. In such a case, the filamentary reinforcing material is chosen to be sufficiently rigid to impart the required anchor properties of the bristles formed from the bends.

A spring structure may be provided at one or both ends of the tubular graft so as to assist in retention of the tubular graft against the wall of the artery in which the graft is in use located.

An example of reinforced graft comprises a tubular body formed of flexible graft material, and a filamentary reinforcing material secured to the graft material in a pattern such that the filamentary reinforcing material extends around the tube and longitudinally thereof to allow the thus-reinforced tubular body to bend, wherein the pattern is defined whilst the filamentary reinforcing material is being secured to the graft material. This can be achieved before the tubular body is formed from a sheet of the graft material as described above, or it may be achieved by securing the filamentary reinforcing material to the pre-formed tubular body. The pattern may be a helical arrangement of the filamentary reinforcing material around the tubular body, or it may be a sinuous arrangement as described above. A sinuous arrangement where opposed bends are overlapped and interdigitated (see below) can assist in imparting columnar strength to the tubular body.

Typically in the embodiments described herein the reinforcement does not constitute a stand-alone stent.

Another aspect of the present invention comprises a graft which is sufficiently axially compressible that once the proximal part is deployed, the distal part can be repositioned prior to its deployment. The position of the distal part can be positioned independently of the position of the proximal part, provided that the distance separating the landing sites of the proximal and distal parts does not exceed the length of the implant.

BRIEF DESCRIPTION OF THE DRAWINGS

Various embodiments of the present invention are described below, by way of example only, with reference to the accompanying drawings, in which.

DETAILED DESCRIPTION OF PREFERRED VERSIONS OF THE INVENTION

In the preferred embodiments described below, the graft comprises a textile polymer sheet which can be either flat or preformed into a tube. The sheet is subsequently reinforced by attaching one or more lengths of fine wire to the material, either by stitching to the surface, threading through pockets formed in the material, threading the wire through the body of the material by weaving, braiding or knitting the wire into the body of the material at the time of manufacture.

A convenient method of rapidly applying the wire to flat fabric described in detail below, is by the use of a computer controlled embroidery machine which is used to form stitches over the wire and attach it to the fabric. This technique is restricted by available machinery to flat fabric which is subsequently rolled and joined to form a tube.

Alternative methods of construction allow the wire to be attached to tubular devices, obviating the need for a join along the length of the device. Such joins have been implicated in longer term failures of some implants.

The pattern in which the wire is laid on the fabric is important for achieving satisfactory mechanical characteristics. The wire is arranged to run approximately circumferentially around the graft, and approximately perpendicular to the long axis of the device. The wire is placed along the length of the graft and each approximately circumferential section can be connected to other circumferential sections so that, in the limit, the entire graft can be reinforced by a single wire.

The intervals between each successive approximately circumferential turn are significant for it is between these parts that the fabric of the graft can produce small buckles, allowing the overall graft to be bent and folded without collapsing the cross-section.

Figure 1:
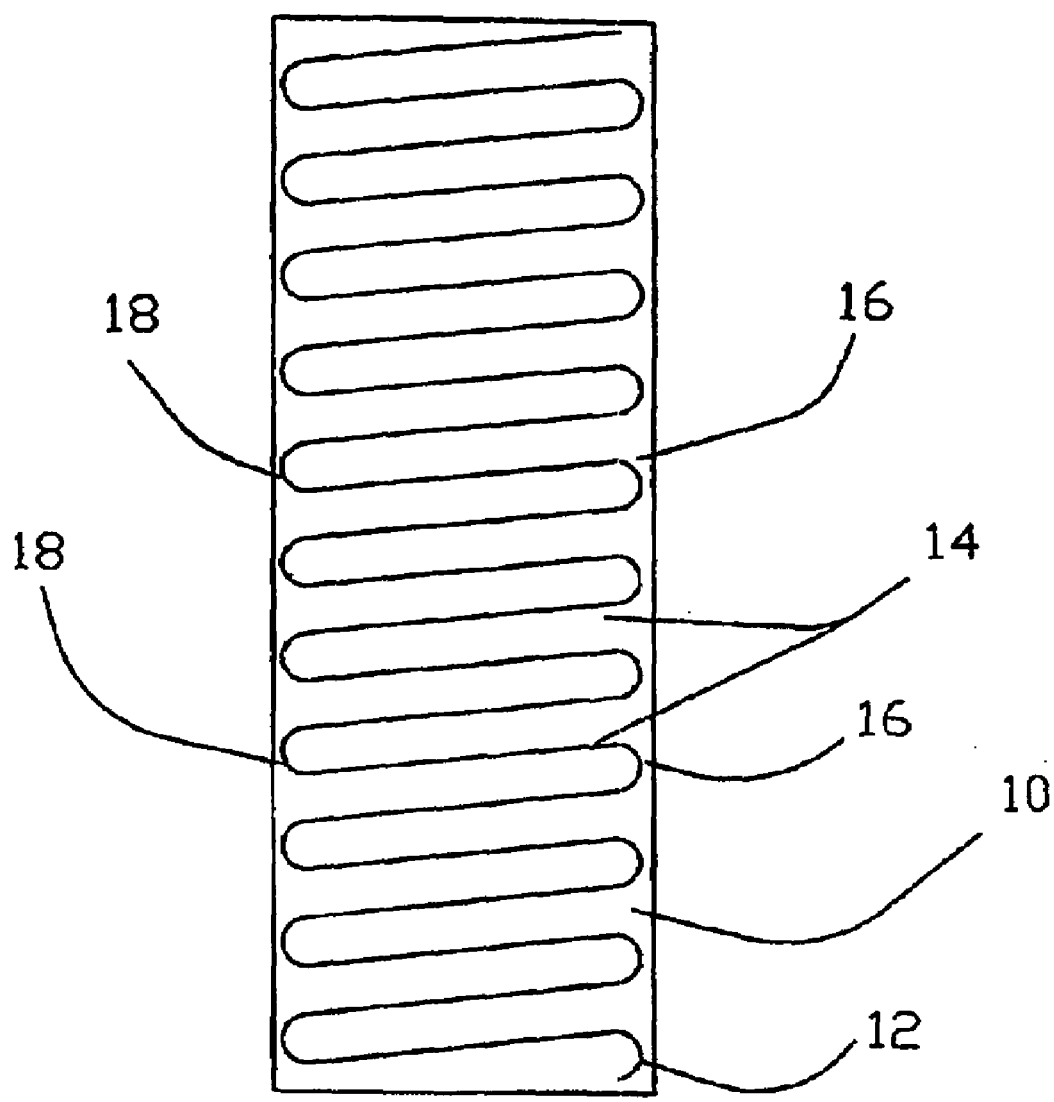
FIG. 1 is a schematic diagram of a first embodiment of reinforced graft prior to rolling into a tubular shape.

Referring to FIG. 1, the embodiment of reinforced graft shown includes a sheet of fabric 10 of the type used for grafts. Onto this sheet 10 is laid a wire 12 which is preferably pre-arranged in a substantially flat ladder pattern in which the straight portions 14 of the wire 12 may lie either perpendicular to the longitudinal axis of the sheet 10 or at a slight angle to the normal to this axis.

Figure 3A:
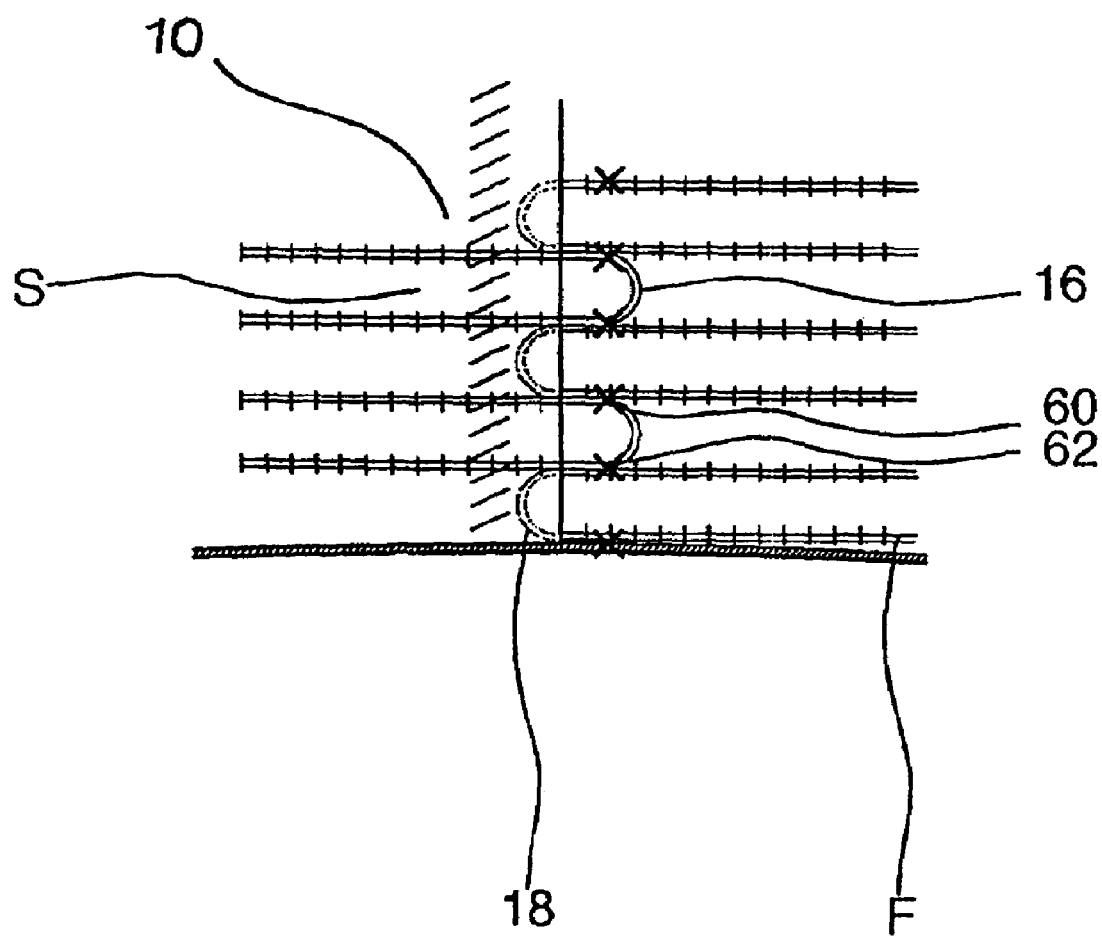
FIG. 3a is a schematic diagram of part of the graft of FIG. 1 or FIG. 2 when rolled into a tubular or frusto-conical shape.
Figure 3B:
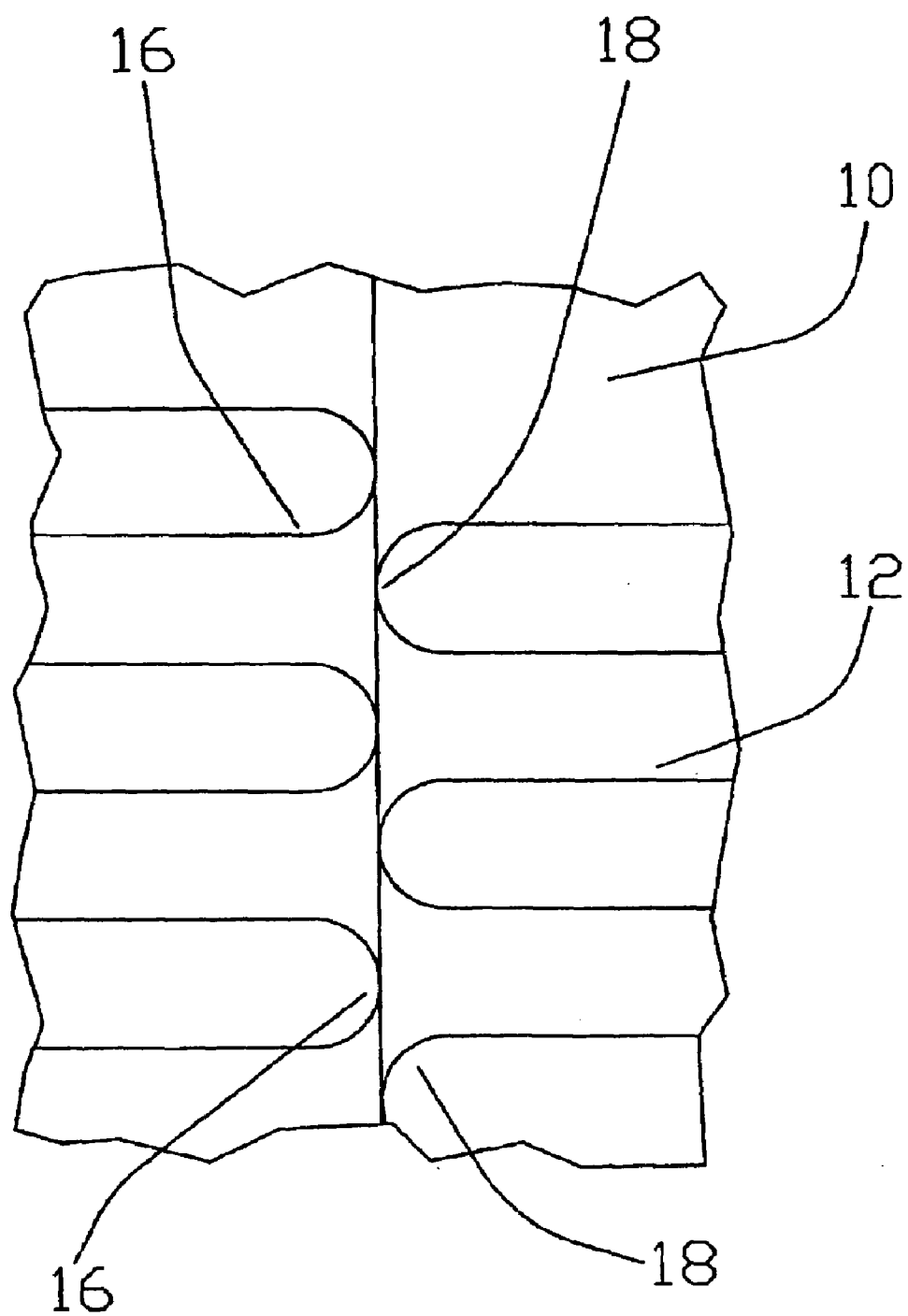
FIG. 3b is a schematic diagram similar to FIG. 3a, showing interdigitation of adjacent rung ends.

The embodiment as shown in FIG. 1 is in use rolled into a tube such that the opposed rounded ends 16, 18 of the wire ladder 12 become located adjacent to one another. When the straight portions 14 of the wire lie perpendicular to the longitudinal axis of the sheet 10, the rounded ends 16, 18 of the wire 12 interdigitate, as can be seen in FIGS. 3a and 3b.

This is described in further detail below.

On the other hand, when the straight portions 14 of the wire ladder 12 are disposed at the appropriate angle to the perpendicular, the opposing rounded ends 16, 18 can be made to oppose or overlap one another, in the manner shown in FIGS. 6a and 6b, also described in further detail below.

Figure 2:
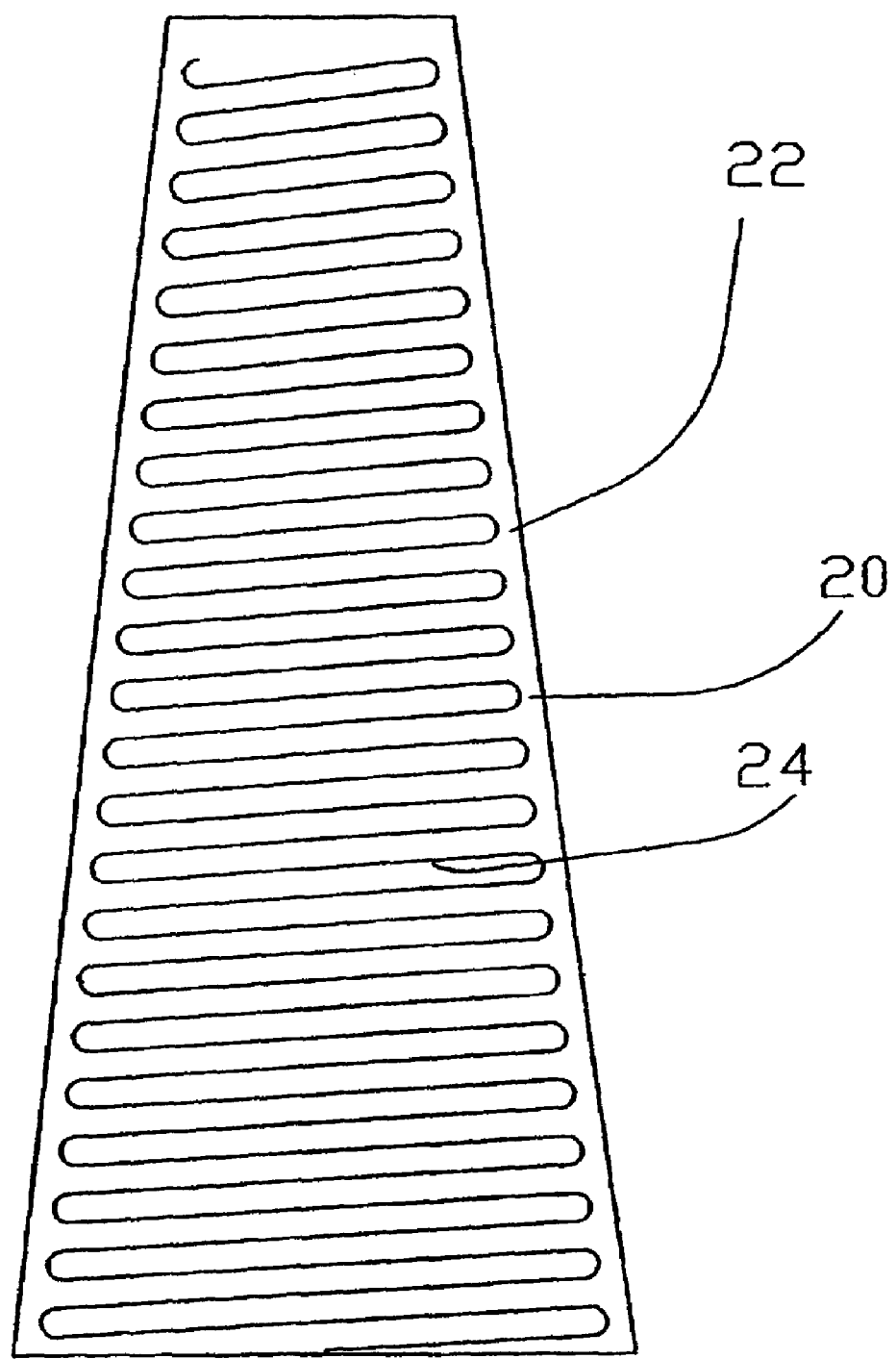
FIG. 2 is a schematic diagram of a second embodiment of reinforced graft prior to rolling into a frusto-conical shape.

FIG. 2 shows another embodiment of reinforced graft which includes a sheet of graft material 20 which tapers from one end to the other in a longitudinal direction of the sheet 20 and a wire 22 of reinforcement material configured in ladder-type fashion and which tapers in a similar manner to the sheet 20.

The straight portions 24 of the reinforcement wire 22 can lie perpendicular to the longitudinal axis of the sheet 20 or at a slight angle thereto, in a similar manner to the embodiment of FIG. 1, so as to produce the effects shown in FIGS. 3a, 3b, 6a and 6b.

Figure 4:
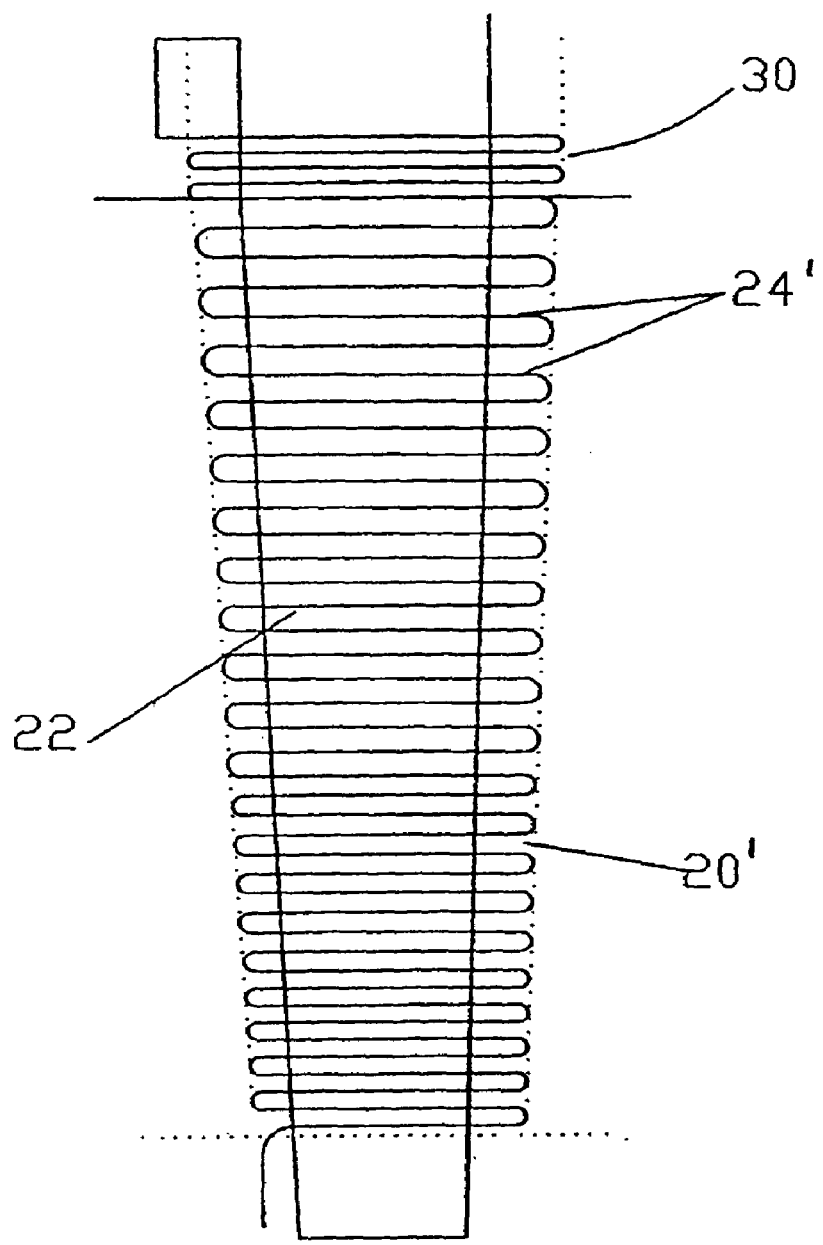
FIG. 4 is a schematic diagram of another embodiment of reinforced graft prior to rolling into a frusto-conical shape.

FIG. 4 shows an embodiment of reinforced graft similar to that of FIG. 2, in which the straight portions 24' lie perpendicular to the longitudinal axis of the sheet 20' and in which at the wide end of the sheet 20' there is provided a portion 30 of wire 20' in which the individual "rungs" have a much tighter pitch. This produces a stiffer opening into the graft.

Figure 5:
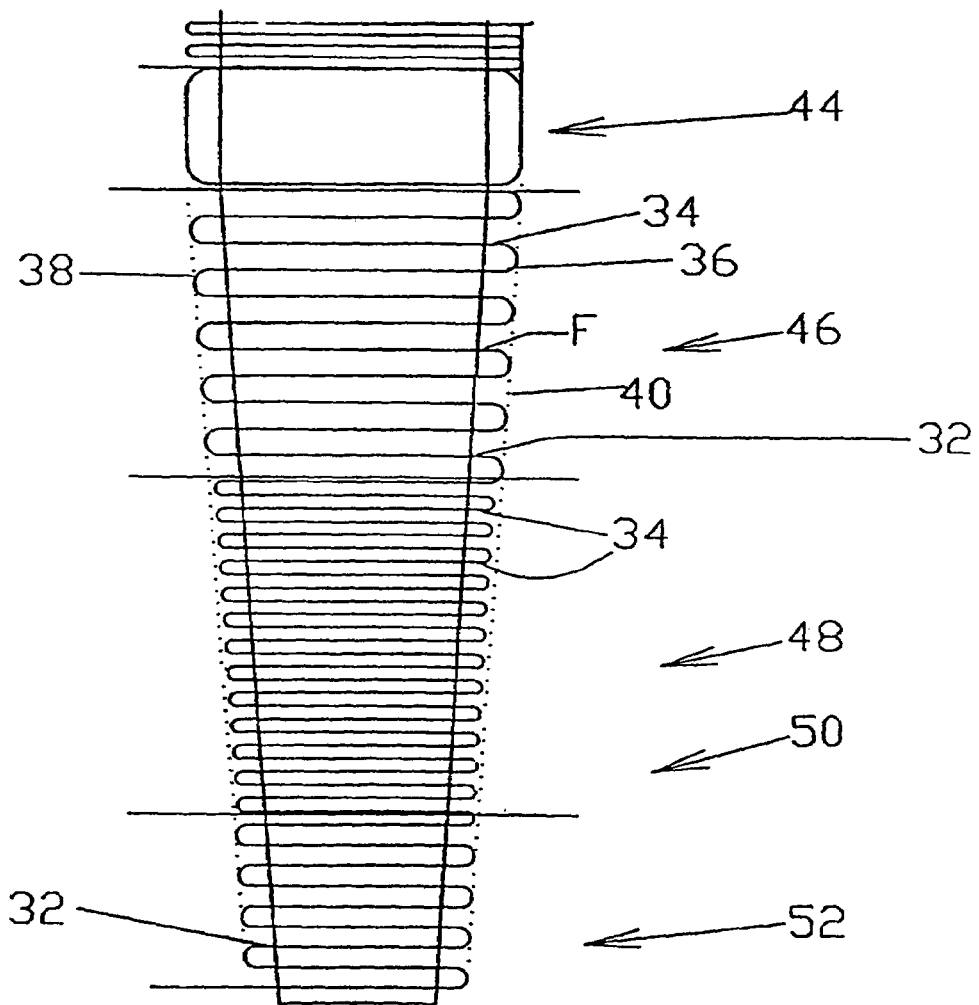
FIG. 5 is a schematic diagram of another embodiment of reinforced graft prior to rolling into a frusto-conical shape.

In the embodiment of FIG. 5, the reinforcing wire 32 is embroidered onto the sheet material 40 as a sinuous pattern which extends over the length of the sheet 40 between the spring elements provided by the wire 32. The sinuous pattern comprises a multiplicity of linear regions 34 which are mutually approximately parallel and which extend laterally of the sheet 40 between the side edges of the sheet. The spacing between these linear regions 34 is greater in the upper wider part of the sheet material 40 than in the narrower part.

Adjacent linear regions 34 are joined together alternately by semi-circular bends 36, 38 disposed adjacent the side edges of the sheet 40.

When the sheet 40 having the reinforcement wire embroidered thereon is bent to form a tube, the wire 32, as in the embodiments of FIGS. 1, 2 and 4, is on the outside of the tube. The now-adjacent side edges of the sheet are stitched together to form a seam which is folded so as to lie inside or outside the tube so that adjacent bends 16, 18 on opposite sides of the seam can be secured together by knotting using ties.

Thus, in this embodiment, the linear regions 34 in the completed tube define a multiplicity of hoops around the tubular graft. These hoops are spaced apart longitudinally of the direction of extent of the tubular graft and thus allow the latter to be bent in a controlled manner without undue kinking at any specific location, thereby mitigating the risk of significant stenosis in use. The end of the tubular graft corresponding to the lower region illustrated in FIG. 5 is of smaller diameter and retains, in this example, a similar ratio of hoop spacing to graft diameter.

The pitch of the sinuous pattern is varied longitudinally of the sheet 40 so that the pitch is greatest in the section of the graft 34 that is to be subjected to the greatest degree of curvature. In section 42 there is a high density pitch to create a collar to hold the neck of the graft fully open and in firm contact with an artery wall. Section 44 is left unreinforced to provide an area for fixation of the graft to the artery wall with an additional fixation device (not shown) Section 46 is of low density pitch where the graft is intended to traverse a relatively straight path through the center of an aneurysm. Section 48 is a transition section with medium density pitch to avoid kinking at the transition to section 50 which is of a high density pitch. At section 50, the graft is required to pass through the most tortuous section of a common lilac artery. Section 52 is of medium density pitch to coincide with that portion of the graft which is intended to lie in the region of the artery which straightens into the external lilac artery. The optimum pitch for any section of the graft is a function of the expected degree of curvature and the diameter at that section.

The fabric used for the graft is standard fabric use in the art, for example micro-fine woven polyester. The wire may be of any suitable filamentary material, such as a nickel/titanium shape-memory alloy (SMA) material, a super-elastic shape-memory alloy material such as that sold as Nitinol. Substances other than shape-memory alloy could be used, the requirements for preferred embodiment being a material which can be deformed to assist insertion of the graft into an artery or other vessel or conduit and which can subsequently return to its un-deformed shape so as to open the graft once inserted.

The advantage of shape-memory alloy is that the graft can be compressed easily for insertion and then allowed to expand to its memorized shape as it heats up to body temperature.

For this purpose, the preferred embodiment uses an equi-atomic nickel/titanium alloy which is triggered at about blood temperature and which in a fully annealed condition is highly ductile. This condition is not typically used in medical devices which commonly employ "super elastic" material (sometimes referred to stress-induced martensitic (SIM) alloy).

The use of a ductile alloy greatly eases handling during manufacture. Preferably, the ductile wire is mechanically polished before integration into the graft.

The preferred diameter of the wire is 0.2 mm to 0.3 mm, although any diameter between 0.15 mm and 0.5 mm can be used.

If the graft is provided with barbs, these need not be of shape-memory alloy.

The thread used to stitch the reinforcement wire to the fabric sheet is preferably a reduced friction coated yarn.

Figure 6A:
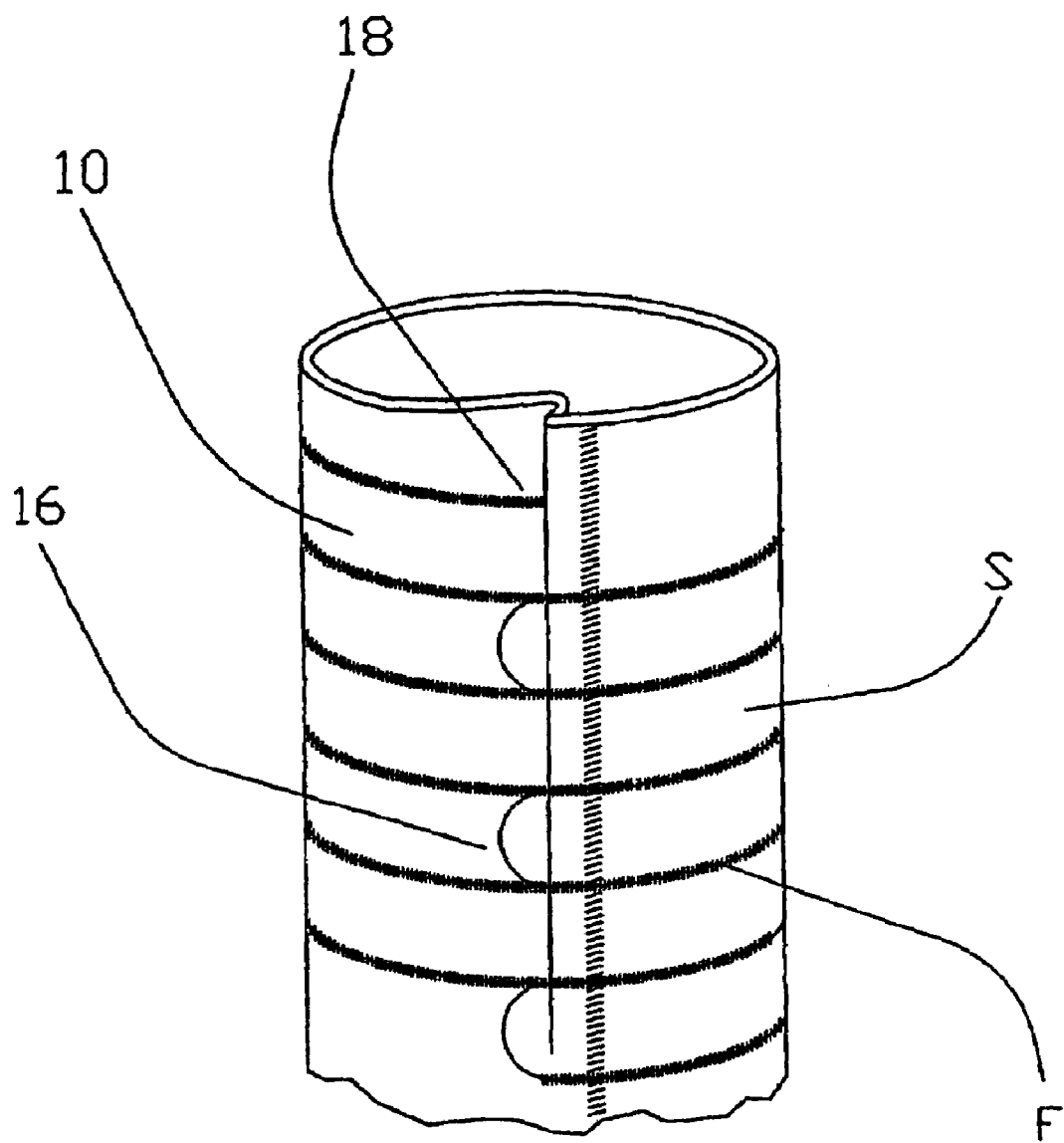
FIGS. 6a and 6b show two different methods of joining a reinforced graft into tubular form with both ends of a reinforcement rung opposing one another.
Figure 6B:
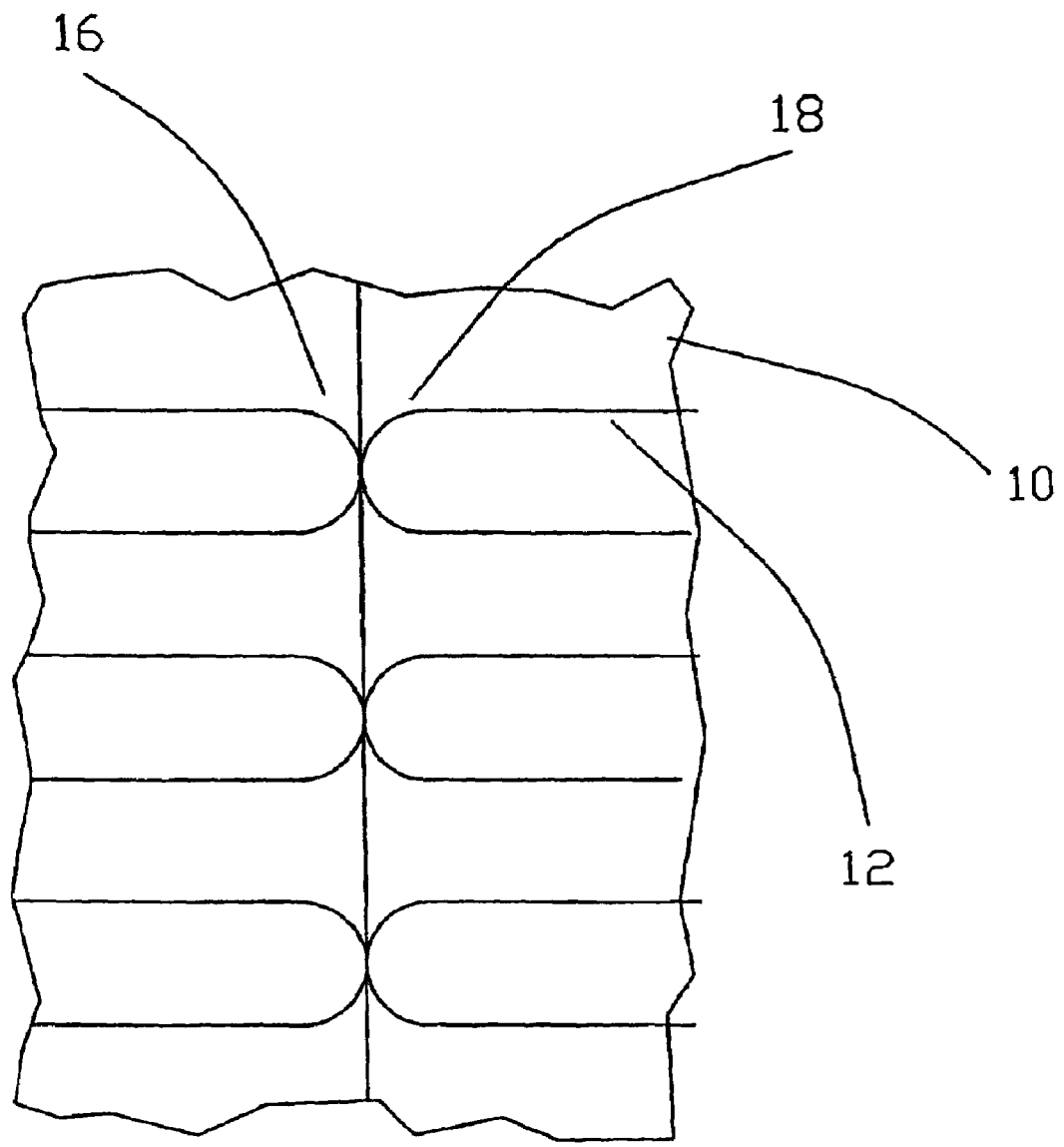
Figure 7:
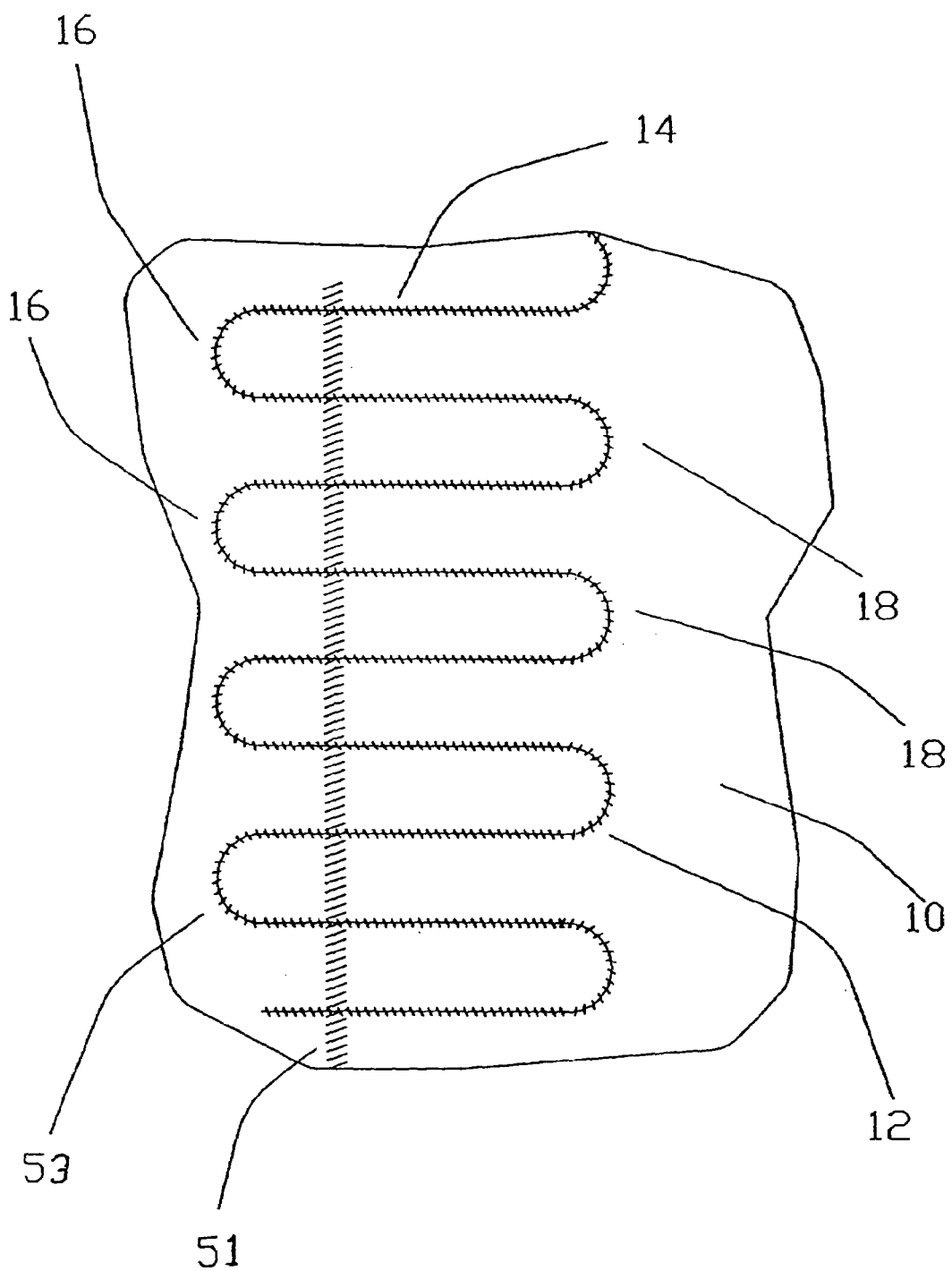
FIG. 7 is a schematic diagram showing a method of stitching a reinforcement ladder lattice.

The preferred method of producing the graft is now described, with reference to FIG. 7 in combination with FIGS. 3a, 3b, 6a and 6b.

As has been described with reference to the embodiments of FIGS. 1, 2, 4 and 5, the sheet material of appropriate shape is preferably laid substantially flat with a single wire of reinforcement material being laid on top of the sheet of fabric. For this purpose, the wire is preferably produced in a substantially planar configuration and, as can be seen in the FIGS., can be said to have a sinuous or ladder pattern.

Referring to FIG. 7, a first stitch line 51 is produced close to one edge of the wire ladder 12. Once this line of stitches is produced, the wire 12 can be moved laterally across the sheet 10 for correct location. Once located correctly, the curved ends 16, 18 of the wire are stitched 53, prior to stitching of the substantially straight portions 14 of the ladder rungs.

Usually, shaped-memory alloy wire is heat treated in the shape which is to be its final form. On cooling, the wire is ductile and easily deformed but on warming to body temperature, the wire reverts to the form which it has been "taught". In the preferred embodiment, however, no such "teaching" is involved, apart from the planar shape of the wire as originally supplied.

It has been found in practice that on heating the wire, when attached to the graft in the manner described, the graft forms a desired rigid cylindrical shape without the need for precise training of the wire. Moreover, such formation of the tubular graft causes it to be pre-stressed and therefore relatively stiffer than an un-stressed equivalent. This enables the use of wires of smaller diameter.

The ratio of the spaces between ladder rungs to the diameter of the graft is most preferably 1:3. A ratio of 1:2 has been found to work, with a ratio for the stiffer parts of the graft being preferably around 1:9. It has been found that a ratio of ladder rungs to diameter of 1:20 is also possible, sometimes benefitting from the use of a softer graft material.

FIG. 7 shows straight portions 14 of the wire 12 being stitched substantially continuously along their length. In order to allow for slight buckling of the graft to pass through catheters and to fit arterial curves, the stitches are preferably loose. This can be achieved by reducing stitch tension, increasing stitch size and/or using a reduced friction coated yarn. The preferred embodiment uses an increased stitch size and it has been found that a stitch size around three times the diameter of the wire is suitable although stitch sizes between six to nine times the diameter of the wire have also been used.

Another feature which can lead to different graft characteristics is the orientation of the wire rungs relative of the weft or warp of the fabric. More specifically, when the straight portion 14 of the wire 12 lie parallel to the weft or warp of the fabric sheet 10, the graft becomes substantially stable. On the other hand, when the straight portions 14 of the wire 12 are oriented so as to lie at an angle, for example 45°, to the weft or warp of the fabric sheet 10, the graft becomes more deformable. Alternatively or additionally, the fabric sheet 10 could be elasticated.

Stitching is preferably carried out by means of a computer controlled embroidery machine of the type particularly used to embroider insignia, badges and logos on uniforms, leisure wear and promotional garments. These machines have the advantage of being fast and providing reliable repeatability. However, manual stitching techniques can also be employed.

It is also envisaged that with computer controlled embroidery and by the design of the graft of the preferred embodiment, it would be possible to design specific grafts by CAD/CAM techniques, thereby considerably facilitating the production of custom implants.

Once the reinforcement wire 12 is sewn to the fabric sheet 10, the sheet 10 is then rolled along its longitudinal axis to form a tube, with the opposing curved ends 16, 18 of the wire 12 moving so as to be located adjacent one another. Once rolled, the longitudinal edges of the sheet 10 are sewn together.

In FIGS. 3b and 6b, the edges of the sheet 10 are sewn such that the curved ends 16, 18 of the wire 12 do not overlap one another. On the other hand, in the embodiments of FIGS. 3a and 6a, the edges of the sheet 10 are stitched so as to overlap one another and such that the ends 16, 18 of the wire 12 also overlap.

In FIG. 3a, the ends 16, 18 interdigitate, whilst in FIG. 6a the ends 16, 18 overlap in substantial alignment.

As will be apparent in FIG. 3a, there are shown stitches 60, 62 which stitch together the overlapping ends 16, 18 of the wire 12. Similar stitches will be provided in the example of FIG. 6a. The advantage of stitching 60, 62 in the manner shown is that this ensures the graft has a substantially circular axial cross-section, with the stitches 60,62 preventing deformation from the circular shape. Without such stitching, the force produced in seeking to return the wire 12 to its substantially flat shape causes the tube to adopt a pear-shape.

The examples of join shown in FIGS. 3b and 6b can be arranged nevertheless to ensure that the graft is substantially circular in axial cross-section by, for example, bending the ends 16, 18 out of the planar configuration at a radius which would be equivalent to the radius of the graft when rolled into its tubular form.

One feature of having the ends 16, 18 of the wire 12 overlap is that along the seam the graft exhibits a certain degree of longitudinal stiffness. When the ends 16, 18 do not overlap (for example abut one another) this longitudinal stiffness is not apparent. This can facilitate deployments which involve inversion of the section of the graft and can also facilitate an intra-operative adjustment in length of the graft by allowing the graft material between pairs of rungs to vary between being taut and buckled. An example of graft could have the loops interdigitation for the main body of the device and overlapping for the ends where the artery wall provides more natural support to the circular cross-section required from the graft and where an optional adjustment in length may be desirable.

Once set in its tubular form, the graft is substantially ready for use. Other elements may be attached to the graft, as described below.

In the preferred embodiments, the reinforcing wire 12 is located on different sides of the fabric sheet 10. More specifically, in the examples described above, the reinforcement wire 12 has been located on a single side of the fabric sheet 10, in use to be either on the outside or on the inside of the fabric tube once rolled.

However, it is sometimes preferred to have at some portions of the graft reinforcement wires on the outside of the graft and at other portions reinforcement wires on the inside of the graft. This can be achieved by using separate wires or by using a common wire which, during the placement process, it pushed through the fabric sheet 10 so as to be located, respectively, on one and on the other side of the sheet 10.

Stitching can be achieved equally well with the wire on both sides of the fabric sheet 10.

A preferred embodiment has the wire on the inside of the graft at the ends of the graft, where optimum seal is required between the graft and the wall of an artery. In the center portion of the graft, where it is desirable to minimize the potential disruption to the blood flow and maximize the anti-kinking support to the graft material, the wire is located on the outside of the graft tube.

In dependence upon the manner of manufacture of the graft, it may be advantageous to form the graft inside out, the thus formed graft then being everted to its correct configuration.

Similarly, eversion could be deployed to facilitate insertion of the graft into an artery.

Figure 8:
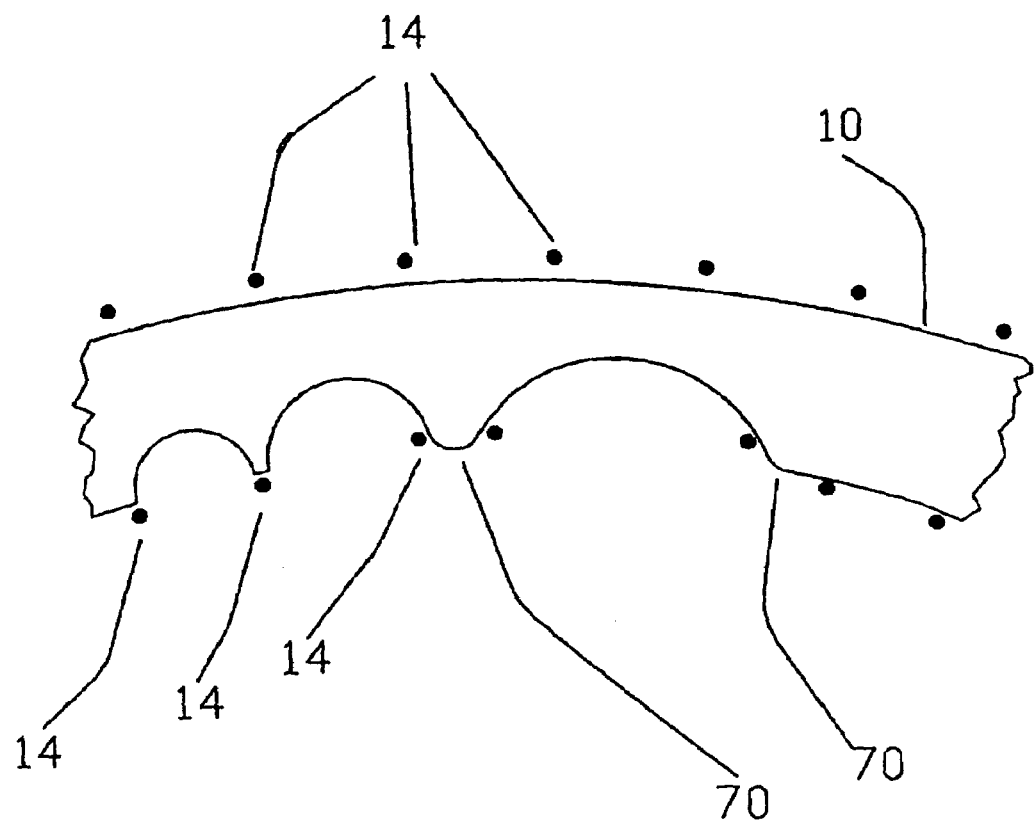
FIG. 8 is a schematic diagram showing the embodiment of reinforced graft of FIG. 1 in a flexed condition.

FIG. 8 is a cross-sectional view of the embodiment of graft of FIG. 1 which is bent into curved fashion. It can be seen that the graft sheet 10 is allowed to buckle 70 slightly so as to allow the graft to curve.

In the preferred embodiment, the entire graft can be wrapped around its own diameter in its longitudinal extent performing a tight curve without collapse or significant kinking.

Once the graft has been formed, it is then inserted into the artery of the patient in a manner known in the art.

In the embodiments which utilize a shape-memory alloy, the graft will be normally cooled to below the critical (trigger) temperature of the shape-memory alloy and compressed radially before it is inserted by the surgeon into position. This gives a compacted graft which may have a folded, star-like cross section which opens out after insertion into the body and heating to above the trigger temperature of the shape-memory alloy to return to a generally circular cross-section. When deployed within the arterial system, the graft should be sufficiently reduced so as not to over-expand, which could potentially damage the artery, but may have sufficient ability to increase in diameter to allow for any increase in size of the aneurysm after insertion. The graft may be located in a catheter or sleeve for insertion along the arterial system to the correct position. The provision of such a catheter or sleeve prevents expansion of the graft before it has been located in the desired position.

Typically, the graft will be introduced into the patient by means of a catheter which is cooled to allow the reinforcing wire of the implant to remain below body temperature and therefore ductile. The implant is drawn through the catheter to the implantation site by means of a pusher wire which is attached to the graft by means of wire or filamentary loops.

It is desirable to have a means of controlled release of the attachment loops so that for instance, a second pusher wire can be introduced next to the first pusher wire, and is attached to the proximal end of the graft. By pushing the second wire and pulling the first wire, the implant can be everted.

Ideally, the entrance to the catheter is of an oval or stellate form so that the implant is crushed in a regular shape to have a smaller external diameter during implantation. Upon exiting the catheter into the blood stream the SMA wire of the graft is warmed and adopts a straighter shape similar to that originally formed in the implant.

Before describing other elements which can be formed on the graft of the embodiments described above, further embodiments of graft are described.

Figure 9:
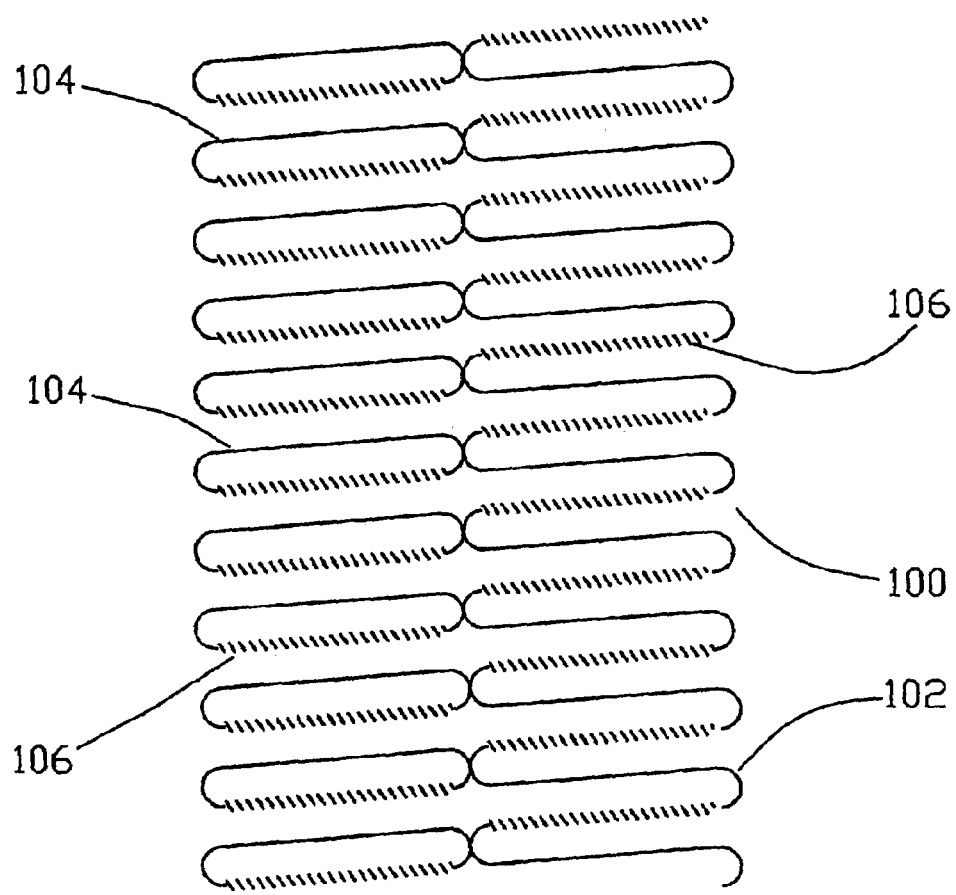
FIG. 9 is a schematic diagram of another embodiment of reinforced graft prior to rolling into a tubular shape.

With reference to FIG. 9, a wire 102 is located on a sheet of fabric 100 such that some portions 104 of the wire are located above the sheet 100, as seen in FIG. 9 and other portions 106 are located below the sheet 100. This is achieved by sequential feeding of one end of the wire 102 into and out of the sheet 100 to provide the pattern shown. The specific pattern shown in FIG. 9 provides two stiffness lines in the longitudinal direction of the graft.

Figure 10:
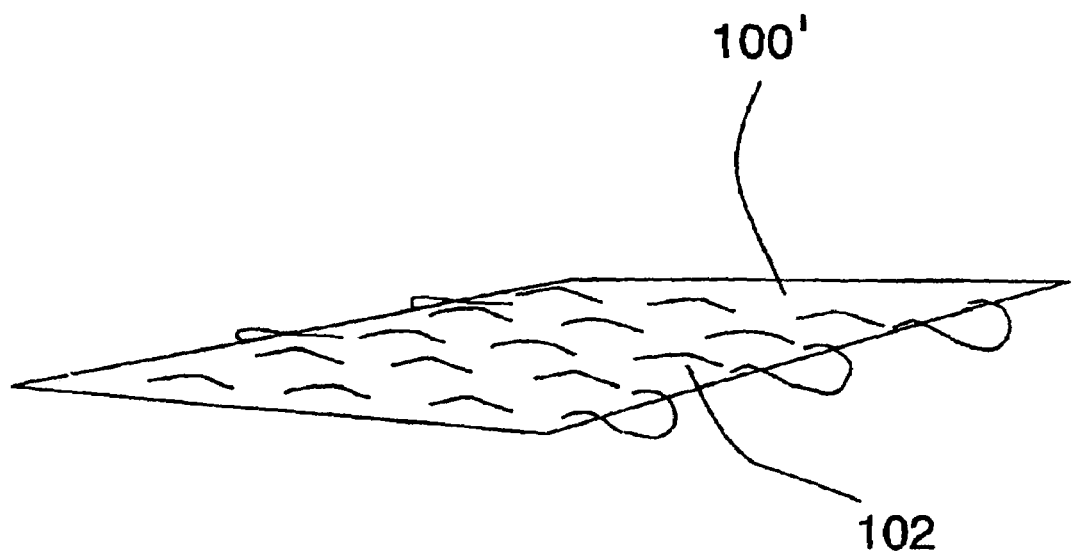
FIG. 10 is a perspective view of another embodiment of reinforced graft showing a wire stitched or woven through a sheet of graft fabric material, prior to rolling.

In FIG. 10, the wire 102 can be seen threaded into and out of sheet 100'.

Figure 11:
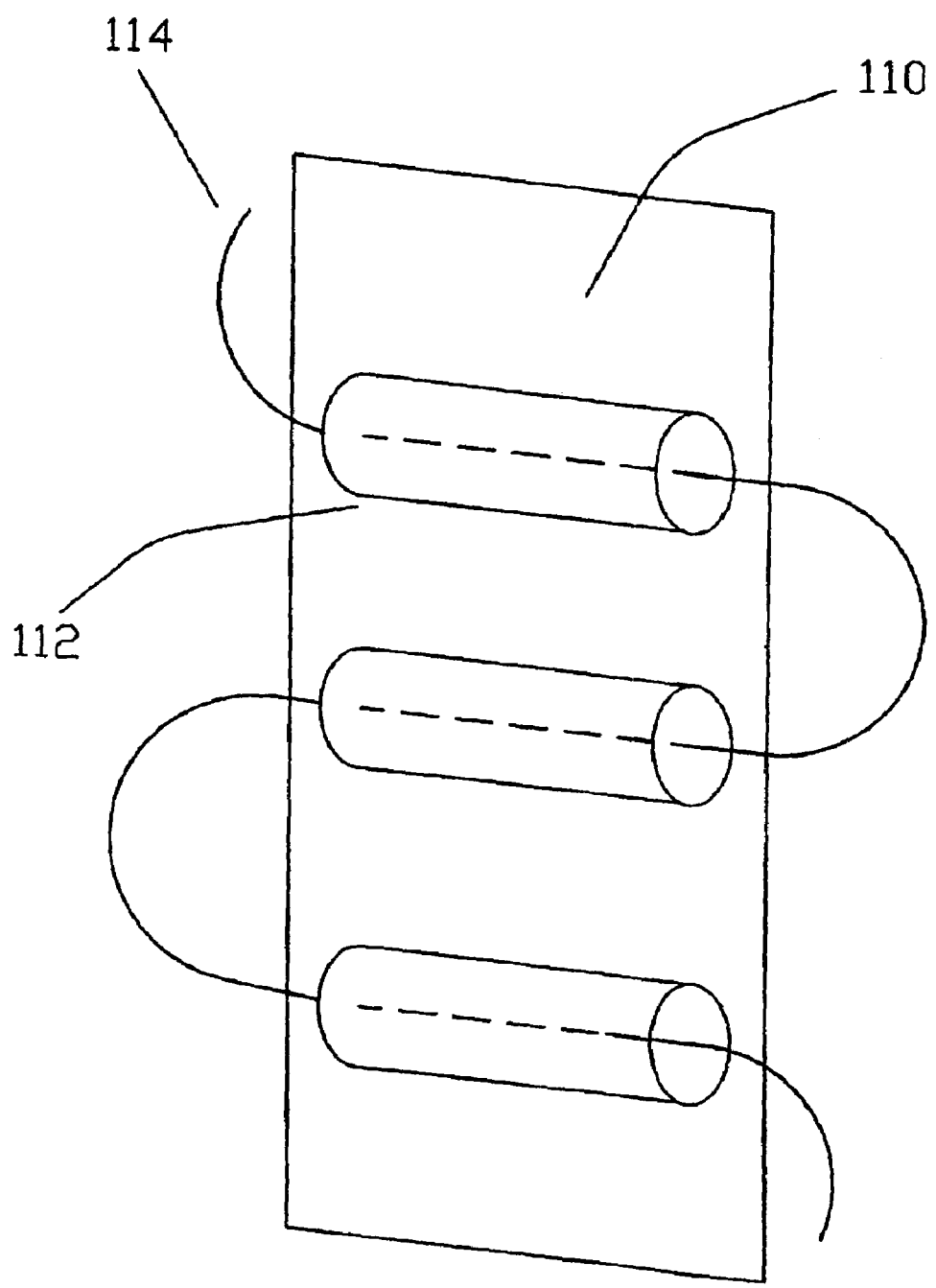
FIG. 11 is a perspective view of another embodiment of reinforced graft.

In FIG. 11, the sheet of graft fabric 110 is provided with a plurality of transversely-extending pockets 112 through which a wire 114 can be threaded. The pockets 112 provide the wire 114 its required shape.

Figure 12:
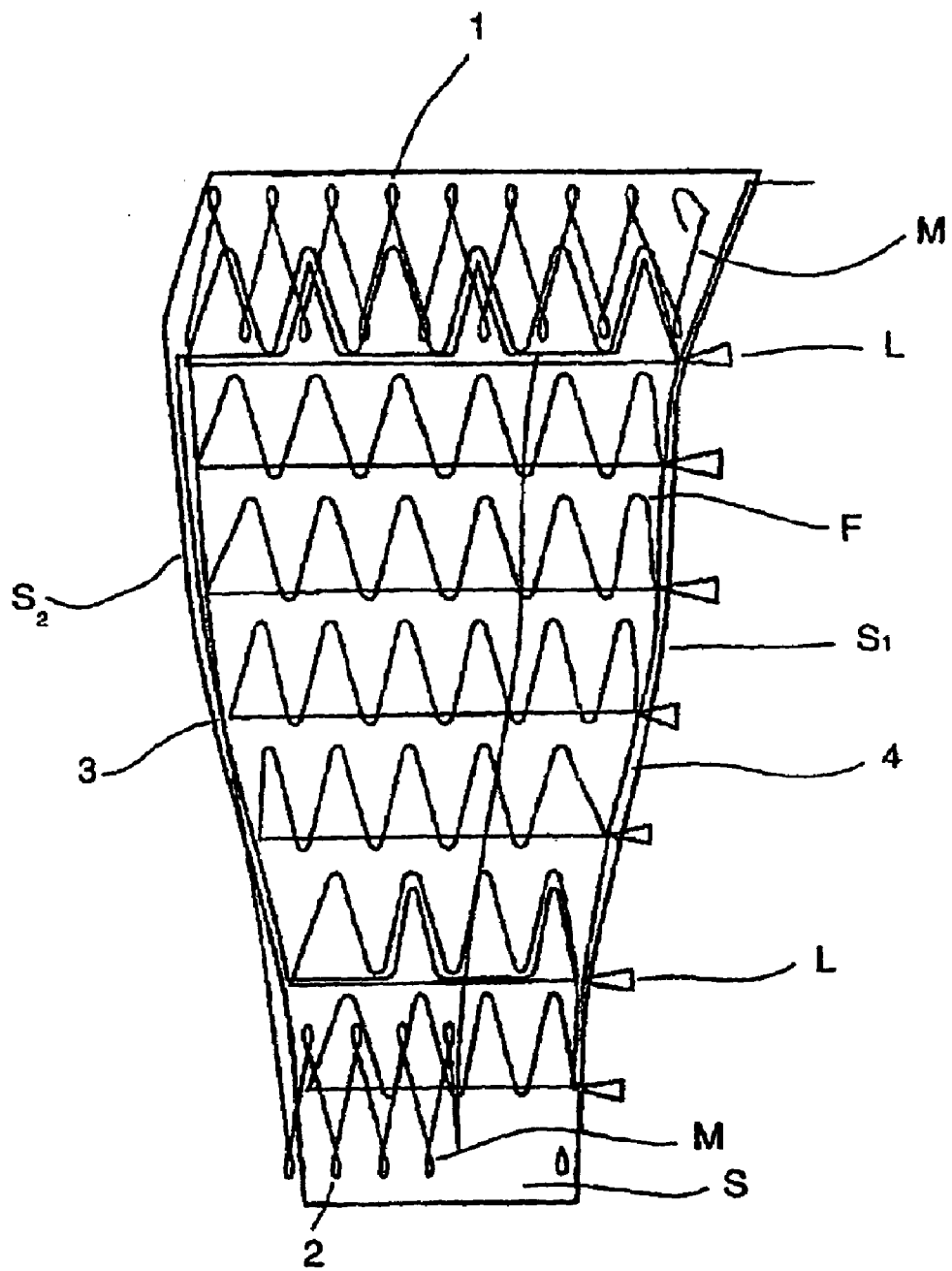
FIGS. 12 to 22 are schematic diagrams of other embodiments of reinforced graft.

In FIG. 12, a woven polyester microfibre sheet S has opposite side edges S1 and S2 tapering inwardly from top to bottom as viewed in FIG. 12 and is shaped so as to enable a tubular graft to be formed which tapers from a relatively wide diameter at one end to a relatively narrow diameter at the other end. The precise shape and size of the sheet S is determined according to the particular configuration of the aortic artery into which the tubular graft is to be fitted.

The sheet S has filamentary reinforcing material F stitched to one surface thereof by means of a computer controlled embroidery machine. The filamentary reinforcing material F is preferably a single filament which is secured to the sheet S so as to define a multiplicity of zig-zag patterns extending laterally of the sheet S between the side edges S1 and S2. The zig-zag patterns are spaced apart longitudinally of the sheet S over substantially the whole of the length of the latter.

The embroidery operation to form the filamentary reinforcing material F to the required shape also defines a series of loops L which project laterally beyond the side edges 1 of the sheet S. The sheet S is also subjected to a further embroidery operation in which a length of spring material M is used to form spring elements at the top and bottom. Each of these springs elements is defined by a zig-zag pattern extending across the sheet S. In forming the zig-zag pattern, the filamentary spring material is looped over at locations typically indicated by reference numerals 1 and 2.

Extending along the side edges S1 and S2 of the sheet are reinforcements 3 and 4 which provide longitudinal stiff pillars imparting lengthwise stiffness and column strength to the graft to prevent it buckling during insertion. The pillars 3 are defined by portions of the spring material M, while the pillar 4 is provided by regions of the filamentary reinforcing material F.

After the structure described above with reference to FIG. 12 has been produced, the sheet material S is folded into tubular form with the side edges S1 and S2 adjacent. These are then stitched together to form a seam and the loops L are secured by suture material to the now-adjacent opposite portions of the respective zig-zag patterns embroidered on to the sheet material S.

The loops at 1 and 2 enhance the properties of the spring.

Figure 13:
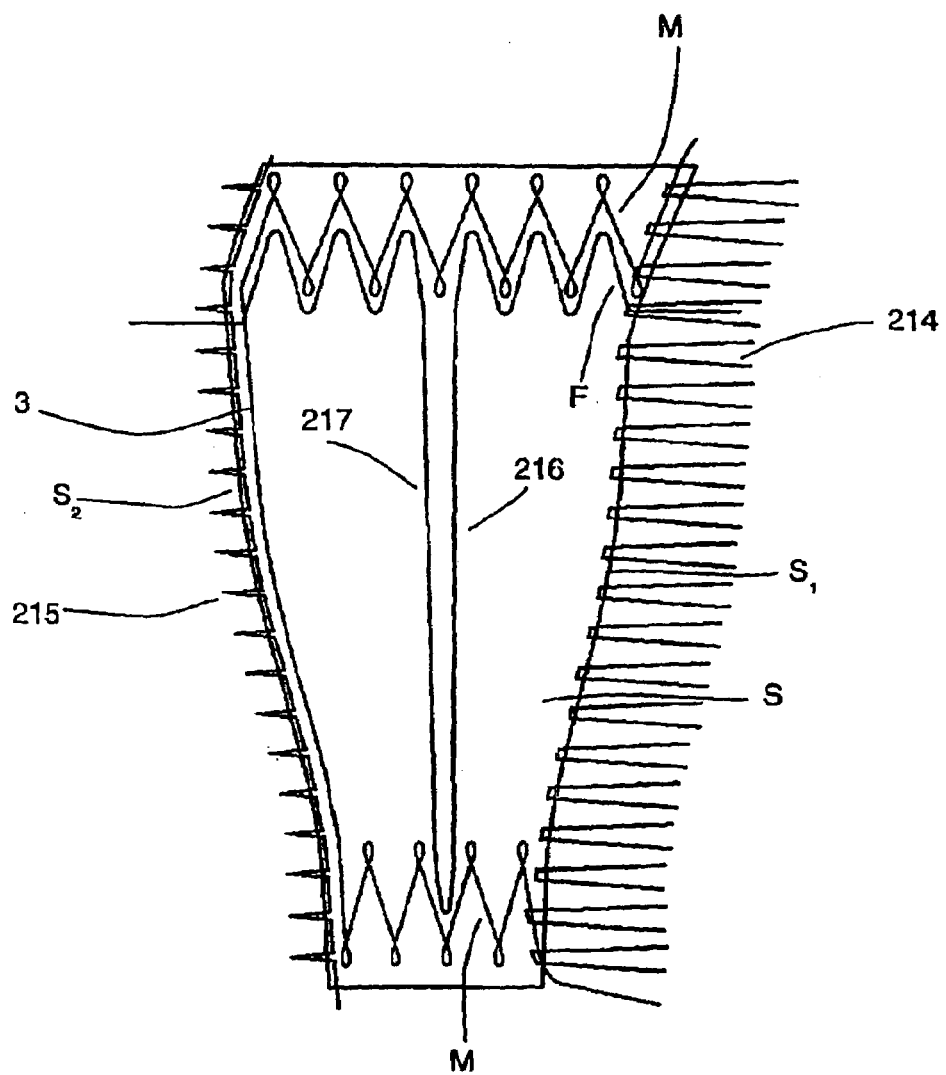

In FIG. 13, the graft is formed with ties 214 which are engagable with respective loops 215 when sheet material S is formed into a tubular shape. In this embodiment, further longitudinal stiffeners 216 and 217 are provided approximately midway between side edges S1 and S2. The ties 214 are knotted to the respective loops 215 to retain the tubular form of the graft.

Figure 14:
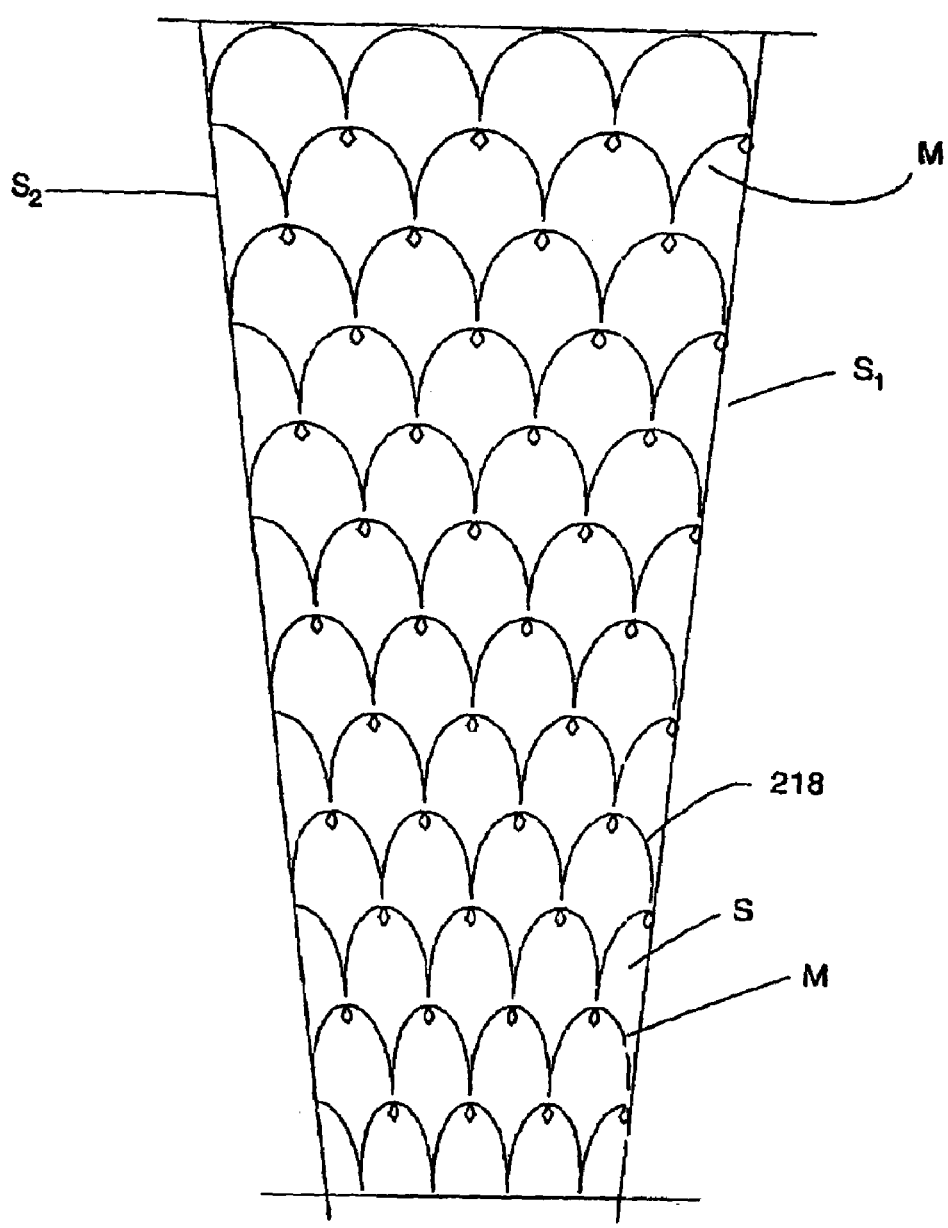

In FIG. 14, elementary spring material M is embroidered onto sheet S to form a series of bends 218 arranged in a fish scale pattern.

Figure 15:
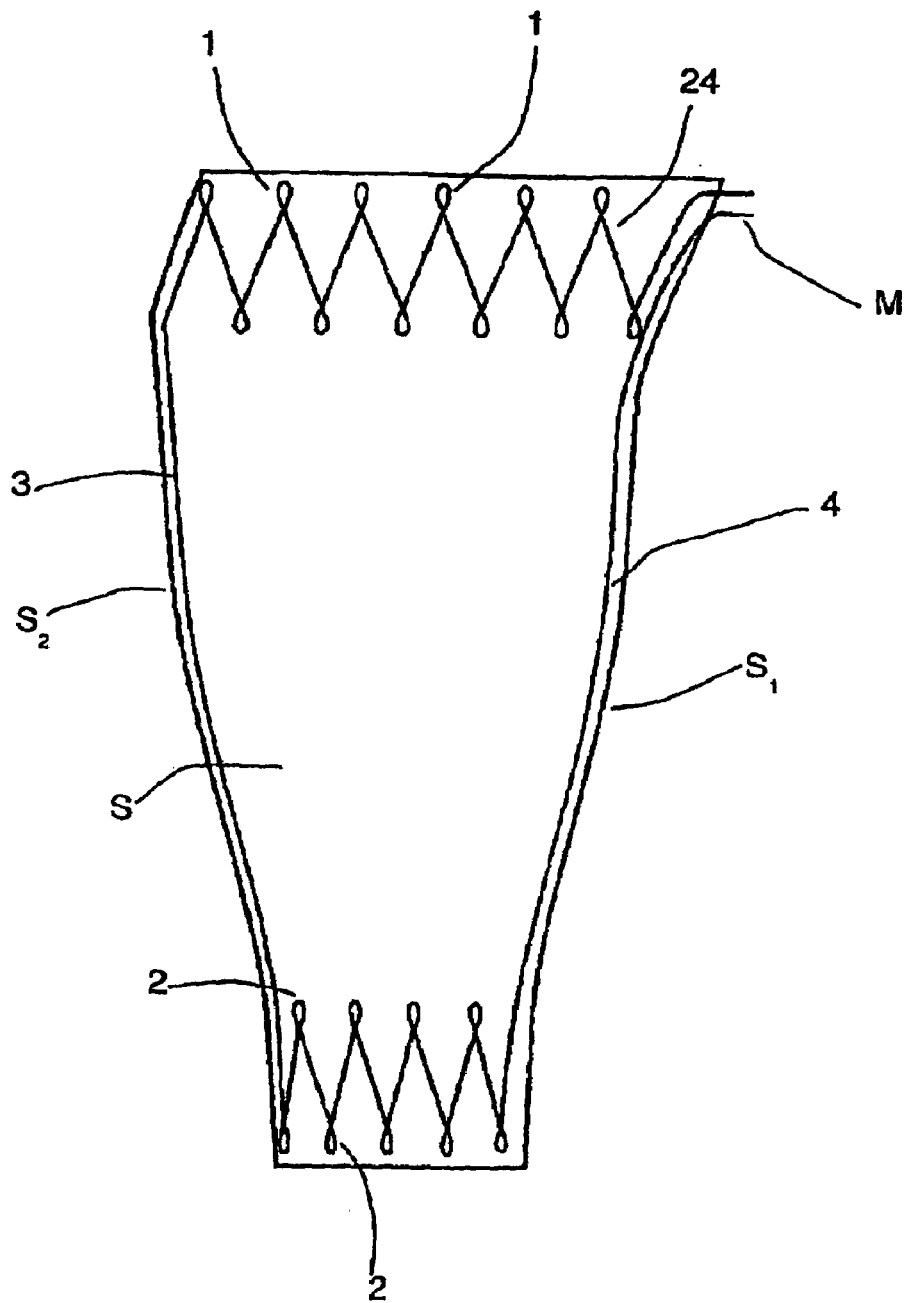

In FIG. 15, there is illustrated another pattern for forming the spring elements at opposite ends of the graft using elongate spring material M. The arrangement is similar to that of FIG. 12, but the path of the embroidery machine is different.

Figure 16:
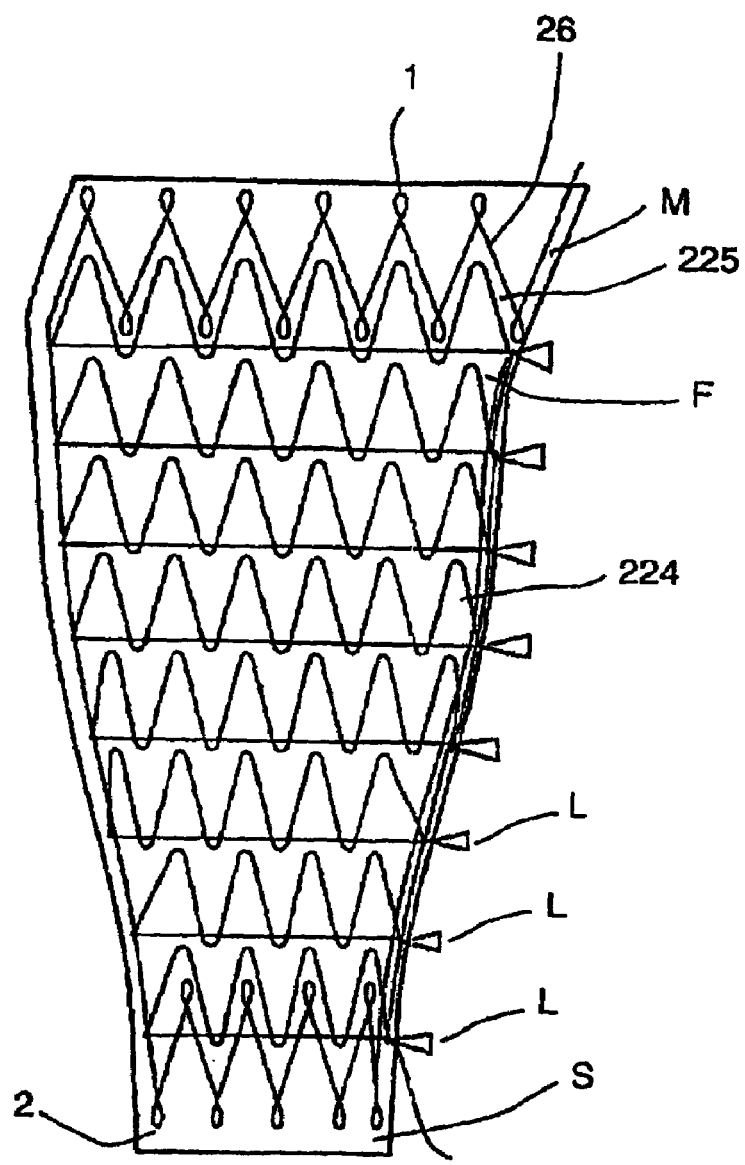
Figure 17:
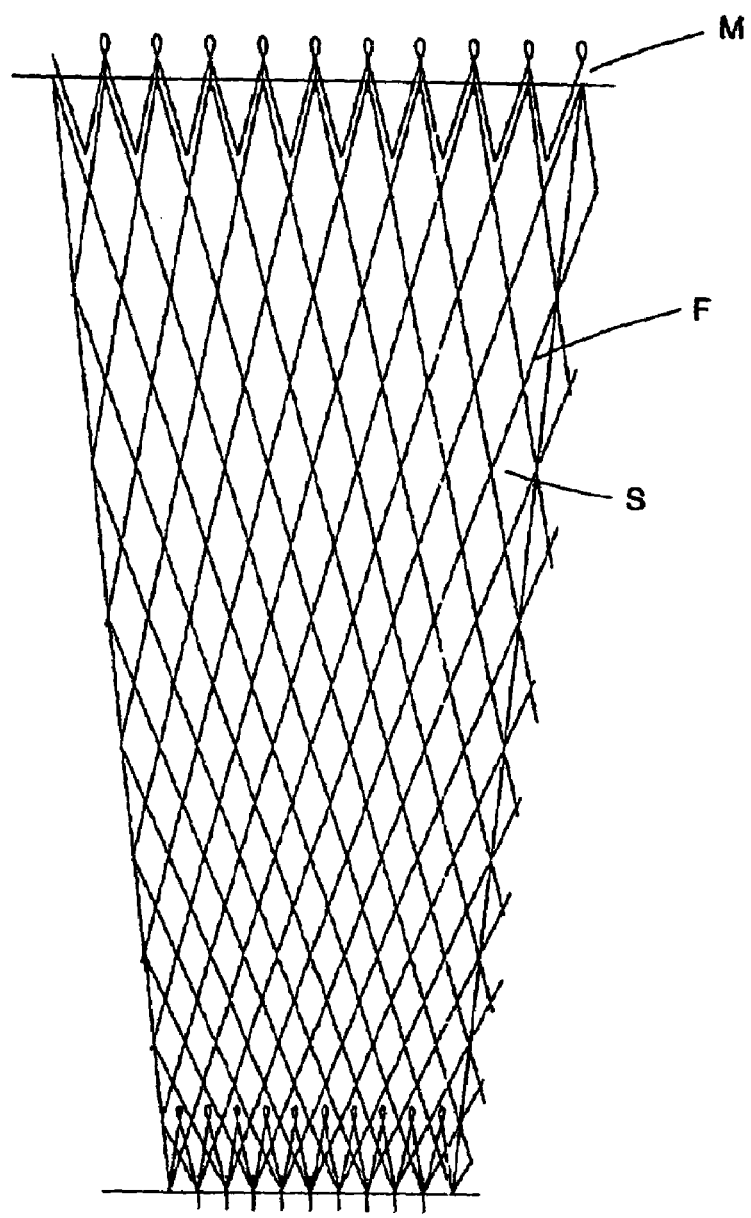
Figure 18:
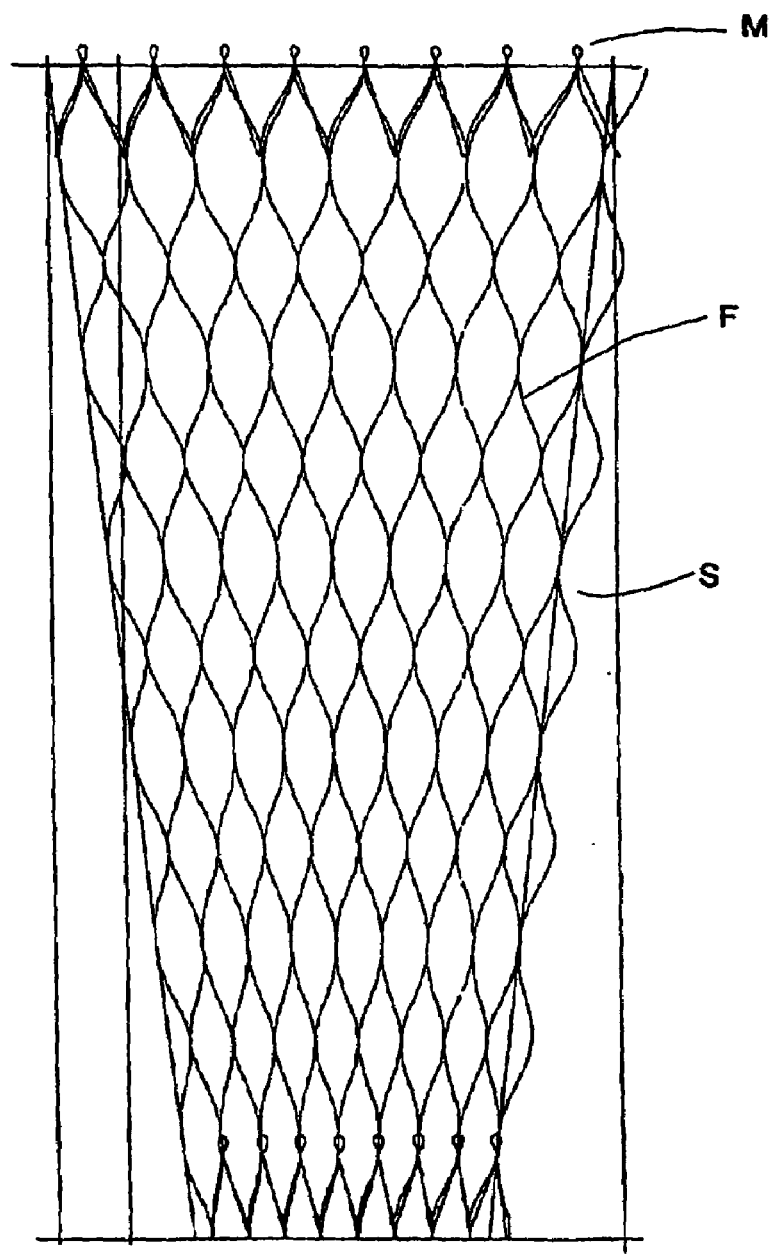
Figure 19:
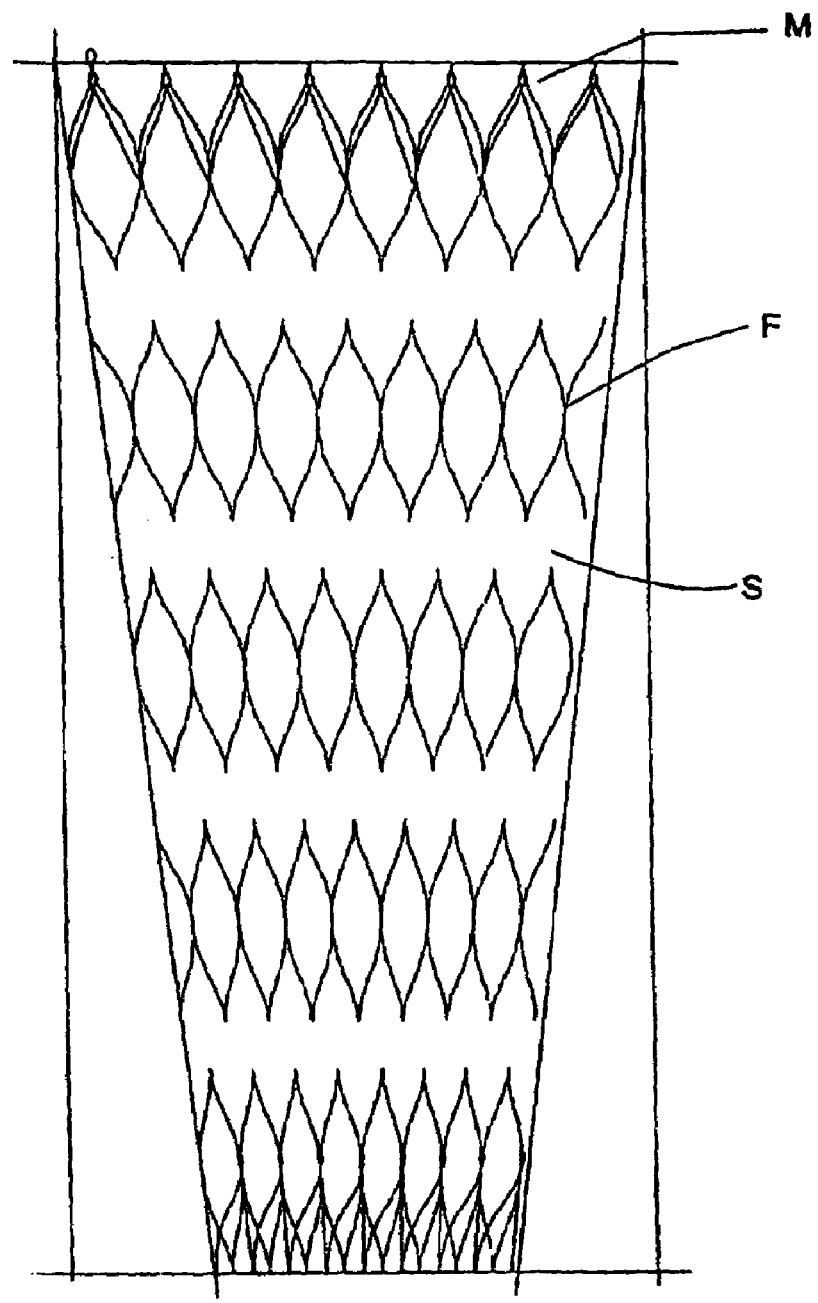
Figure 20:
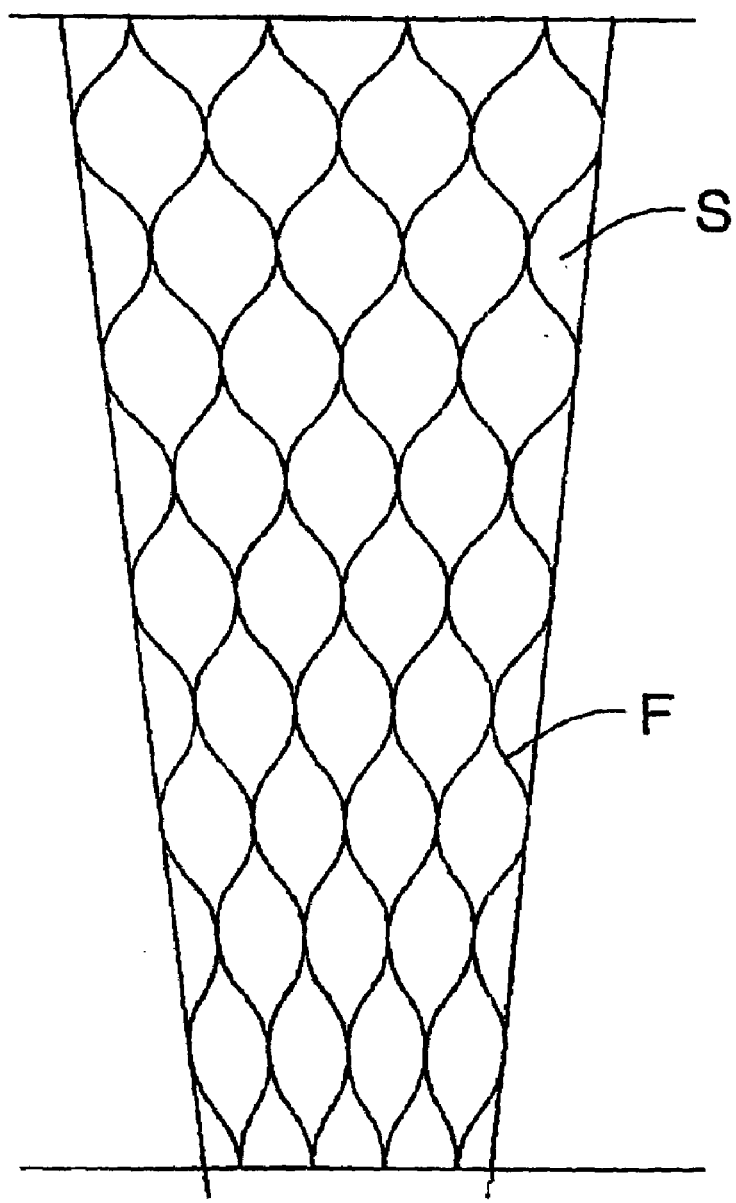
Figure 21:
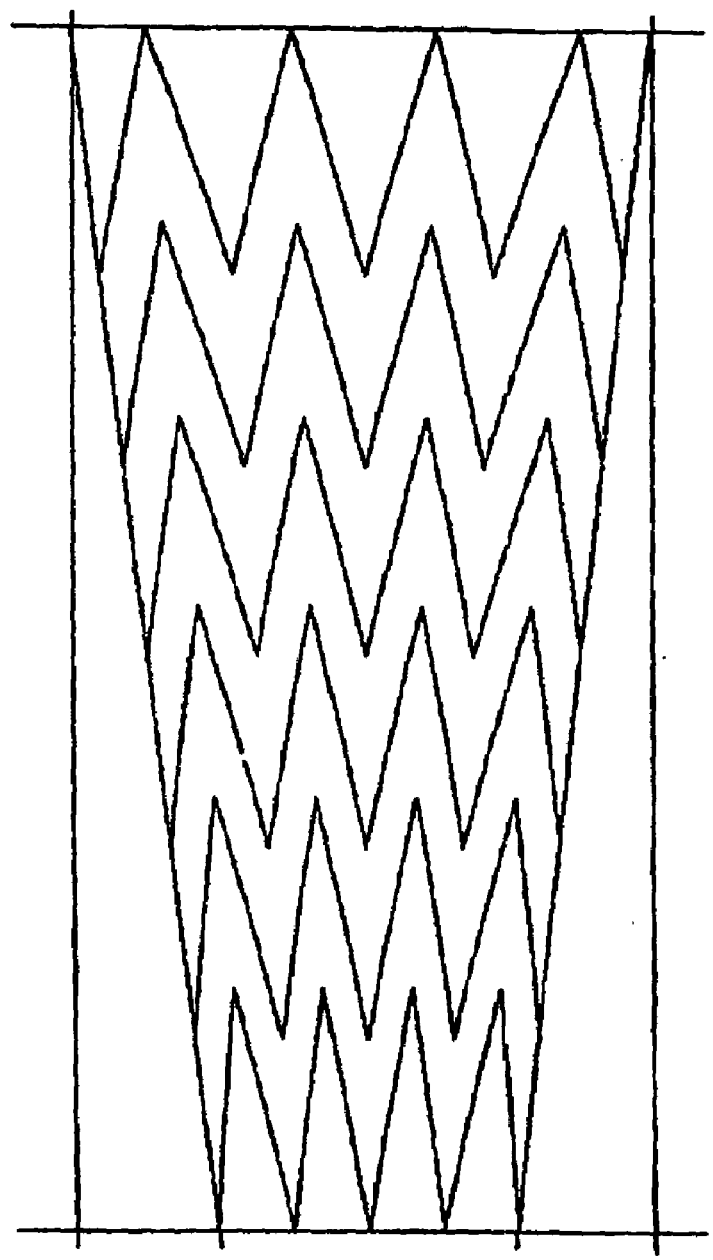
Figure 22:
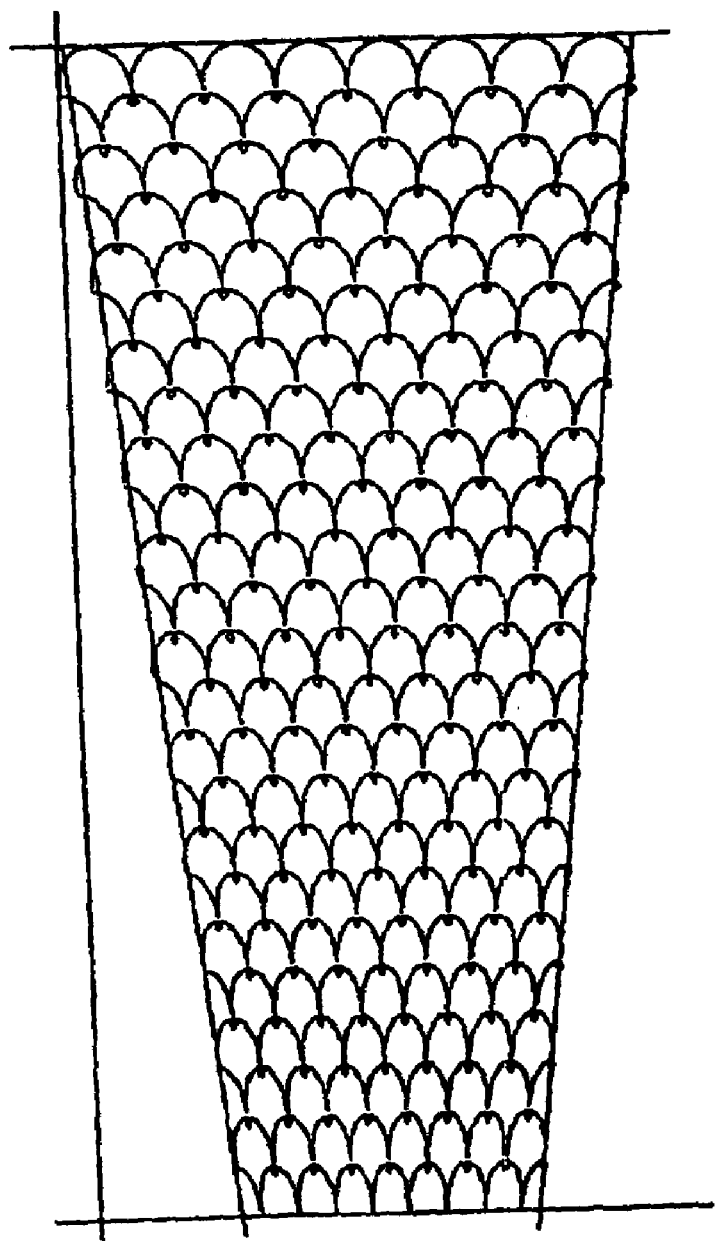

FIG. 16 shows an arrangement also similar to that of FIG. 12.

Pattern 224 of the filamentary reinforcing material F is intermittent down the length of the graft to provide more flexibility. Retention hooks are shown at 225 which assist in retaining the graft in position in the artery in which it is fitted in use. The spring elements at the top and bottom of the graft are defined by the spring material M, and the small loops 1 and 2 are used to assist attachment of these to the sheet S.

FIGS. 17 to 22 show alternative patterns of the filamentary reinforcing material which can also be stitched at selected locations using a computer-aided embroidery machine onto the sheet S in order to provide columnar stiffness combined with radial springiness to hold the lumen open. At the top and bottom of the sheet S are shown looped hook wire arrangements acting to secure the graft in place.

The materials used for reinforcing in the above described embodiments may be any bio-compatible materials suitable for implantation, including nylon, polyester, silk, polyglycolic acid, polylactic acid and metallic wire. The use of monofilament polyester and super-elastic or shape-memory metals alone or in combination is preferred. The use of a super elastic, shape-memory alloy such as Nitinol allows the device to be self-expanding and does not require the use of an additional device (such as a balloon catheter) to expand the generally cylindrical shape from a compressed condition to an extended condition.

Additional elements for the embodiments of graft described above are now mentioned.

The device may be retained in the required position within the artery by use of a multiplicity of retaining bristles or barbs formed from suitably rigid metallic or polymeric material.

These barbs may be arranged to protrude a sufficient distance from the external surface of the tubular graft and when provided in sufficient numbers they will engage within or through the wall of the blood vessel such as to resist movement of the graft under the force exerted by the flow of blood there through.

Figure 23A:
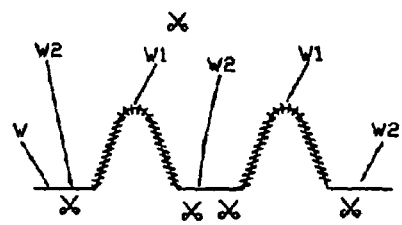
FIGS. 23a to 23f are schematic diagrams showing how barbs can be formed.
Figure 23A:
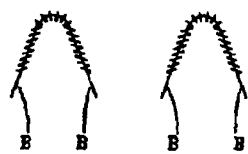

FIGS. 23a to 23f show various arrangements for producing bristles or barbs on the outer surface of the graft at the upstream end thereof relative to the direction of flow of blood therethrough. In FIG. 23a shape-memory alloy wire W is attached to the sheet S (not illustrated in FIG. 23) by stitching the wire using a computer-controlled embroidering machine over spaced bends W1 in the wire W. These spaced bends W1 are spaced apart around the periphery of the tubular graft and are interconnected by intervening regions W2 which are left free, i.e. are not attached by stitching to the sheet S.

Cutting of the wire W at these regions W2 as indicated schematically by the scissors in FIG. 23a results in the formation B in the completed graft. These bristles B point generally in the direction of blood flow through the graft and act as barbs which dig into the wall of the artery to prevent the flow of blood in the aorta, or other forces such as patient movement, from dislodging the graft from its placed position.

Figure 23B:
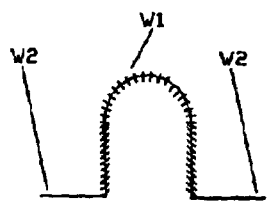
Figure 23B:

As can be seen from FIG. 23b at 180 degree bend W1 will result in the bristles B projecting parallel to the longitudinal axis of the graft. This is optimum for resisting the main force of the blood flow.

Figure 23C:
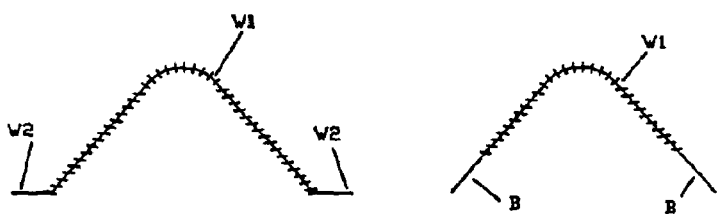
Figure 23D:
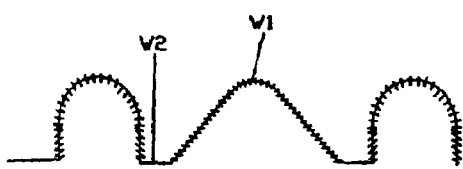
Figure 23D:
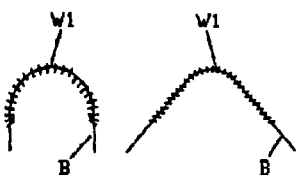
Figure 23D:
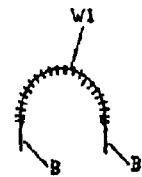

As indicated in FIG. 23c, bends W1 with an angle of less than 180 degrees will result in the bristles B extending at an angle to the longitudinal axis of the graft. This configuration is optimum for resisting torsional forces acting on the graft.

As shown in FIG. 23b 180 degree bends W1 may alternate with bends of an angle less than 1800 to produce combined effects.

Figure 23E:
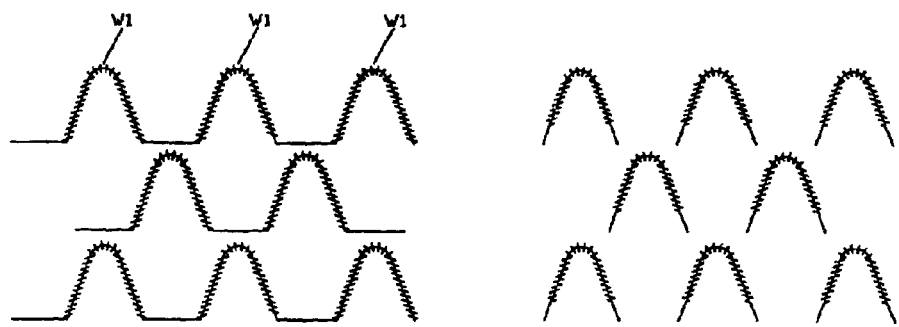

As shown in FIG. 23e there are three rows of barbs arranged in a staggered formation on the external surface of the graft such that there is an optimal variation in the direction of the extent of the bristles B to ensure that a mechanical lock with the wall of the artery is ensured irrespective of the lack of uniformity that is commonly found in arteries.

Figure 23F:
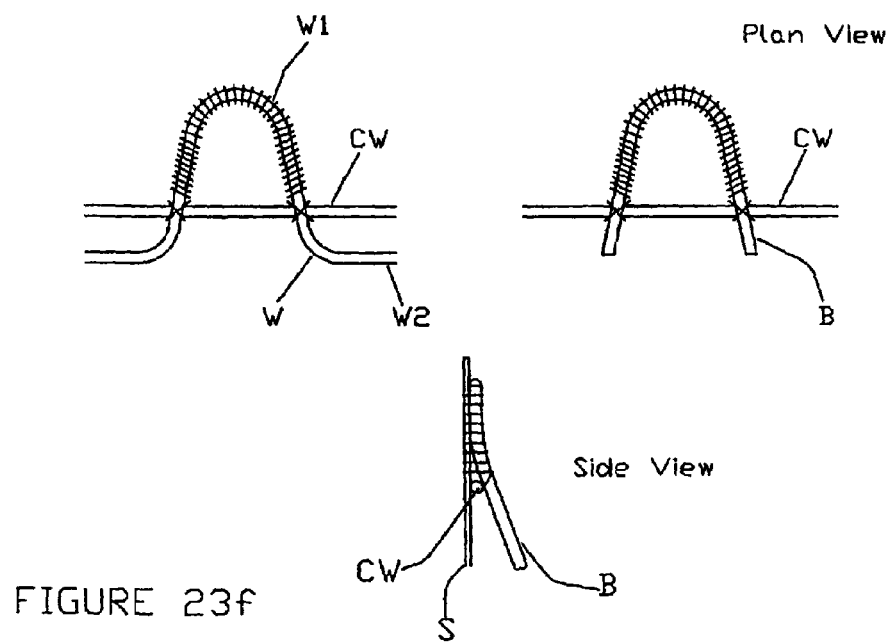

In FIG. 23f there is shown an arrangement where the wire W forming the bends W1 overlies a circumferential wire CW so that the latter is disposed in the region of the junction between the bends W1 and the intervening regions W2. The result of this is that, after cutting at the regions W2, the bristles B protrude at a definite angle from the surface of the sheet S.

Additionally, further stitching may be utilized in the region where the wire W crosses over the circumferential wire CW so as to provide additional anchorage or the bristles B at the points where these bristles protrude from the wall of the tubular graft.

The preferred embodiments also provide for the attachment of radio-opaque elements to the sheet of graft material. The elements are possibly embroidered onto the sheet of fabric.

The preferred radio-opaque element is a fine wire embroidered in a pattern to provide calibrated deformations along its length to provide a radio-opaque length measurement along the longitudinal axis of the graft.

In an alternative embodiment, the radio-opaque elements provide indications of "left", "right", "anterior" and/or "posterior" and may, for example, be in the form of letters designating the first letter of each of these position terms.

In the case of a radio-opaque element, this could be a tantalum or other high molecular number element (opaque) wire embroidered onto the sheet of fabric. Alternatively, the radio-opaque markers could be a radio-opaque ink printed on the fabric, pellets or a sheet of material embroidered over the fabric sheet.

Figure 25:
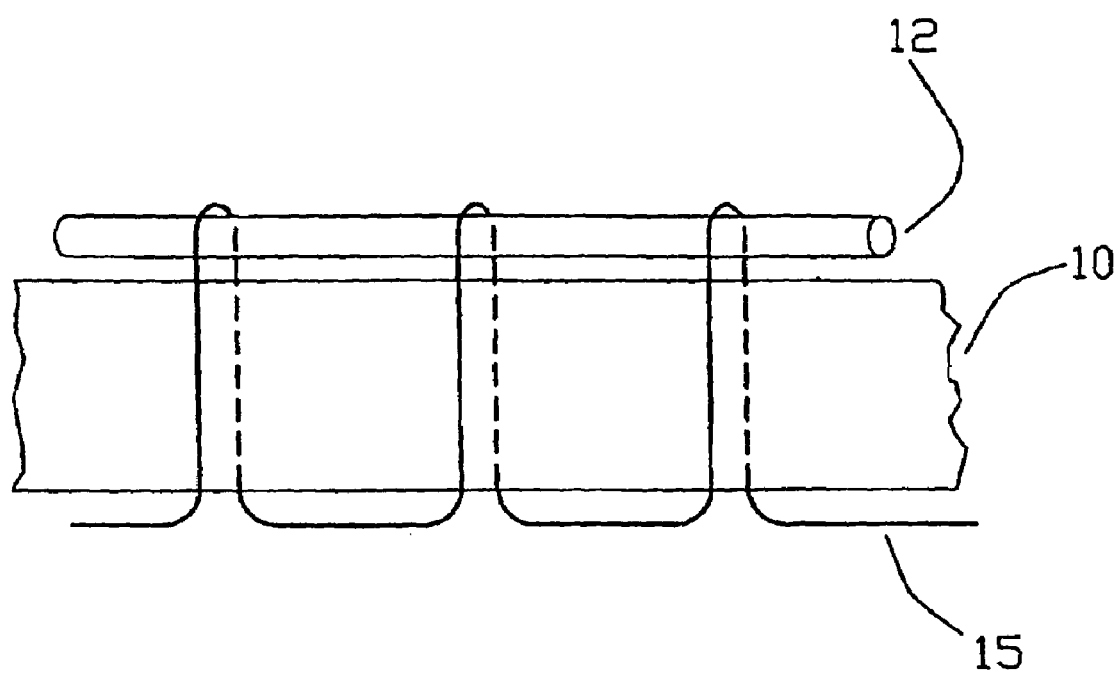
FIG. 25 is a schematic view of a reinforcement wire, barb or radio-opaque element sewn by a sewing machine to a fabric sheet.

The opaque markers, and indeed the reinforcement wire 15" itself or the barbs could be provided on a sewing machine bobbin to be placed on the fabric sheet 10" in a lock-stitch 15, as shown in FIG. 25.

Figures 24A, 24B:
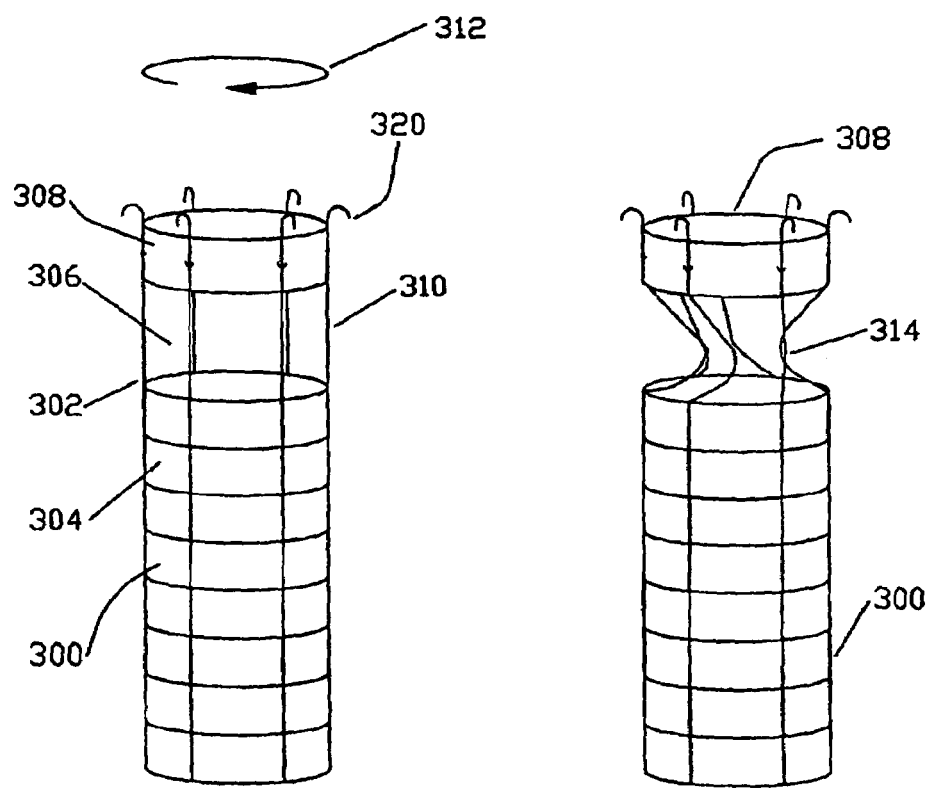
FIGS. 24a and 24b show another embodiment of reinforced graft.

In FIG. 24a is provided an example of graft 300 formed in accordance with any of the above-described embodiments and which has at one of its ends 302 a region 306 not covered by graft fabric 304. Beyond region 306, there is a small annulus 308 of graft material. Between the annulus 308 and the graft 300 there is provided a plurality of struts 310 of shape-memory alloy connecting the graft 300 to the annulus 308. The location 306 allows the graft 300 to be placed between two arteries.

The advantage of the structure shown in FIG. 24a is that the annulus 308 can be rotated, for example in the direction shown in the arrow 312, such that the structure 310 twists to a neck 314 as seen in FIG. 24b. A loose connection between the struts 310 and the annulus 308 assists in this generation of the neck 314. In its twisted shape, the neck 314 can be tied providing a very flexible leading end of the graft 300 by means of the mobility of the annulus 308.

It can be seen in FIGS. 24a and 24b that the struts 310 also provide barbs 320.

In all the described embodiments, the barbs could be separate elements stitched to the fabric sheet. The advantage of this is that there is no risk of weld fractures.

One practical use of the graft of FIGS. 20a and 20b is as a supra-renal fixation element.

It is envisaged that any of the grafts described herein can be used as an occluder by providing a fabric cover over one of the open ends of the tubular graft. Alternatively, the graft could be used as a platform for the deployment of an artificial valve.

The described embodiments facilitate a significant increase in diameter of the graft over a very short axial length while preserving all the desirable attributed of the graft. An embodiment of a graft with such a dramatic change in diameter is for the endoluminal treatment of an abdominal aortic aneurysm with shape of an "Ali Baba's Basket". In this situation there is essentially no neck to anchor onto between the aneurysm and the renal arteries. The graft can be manufactured and deployed such that it is an optimal fit at the point where the renal arteries branch off and then flares out to match the shape of the top of the aneurysm. This graft would be anchored in position primarily with a supra-renal fixation element.

The stitching used to attach the preform to the graft fabric can be varied in order to optimize mechanical characteristics.

Stitches may be triangular or square in order to control the contact area between preform and stitching thread.

The graft may be used in conjunction with a self-sealing element such as an occlusion device. This may be on normal applications of the graft or when used as an occlusion device in conjunction with an occlusion barrier or when used as an artificial vein.

The pattern of preform can be selected in order to create sections along the length of the graft that can vary from being totally flexible to totally supported. In an embodiment used as an occlusion device, two highly supported sections are linked by a highly flexible section which allows the supported sections to deploy perpendicular to the long axis of the vessel irrespective if the tortuosity of the vessel.

The occlusion barrier may be created with a preformed ring of SMA or a circular or spiral pattern that may be embroidered wire or an attached preform in order to improve the seal in a vessel with an irregular cross section.

In all the above-described embodiments, the fabric seam could be produced by sewing, welding, thermal bonding and by use of adhesives.

As noted previously, the invention also involves a graft stent which is axially compressible capable of having its distal end brought closer to its proximal end to shorten the length of the device from its nominal length. Some prior graft stents can sometimes achieve a reduction in length of 10%. Occasionally, tapered devices can be compressed by up to 15%, although this involves significant separation of the stent ring components from the graft material as well as wrinkling and kinking of the graft material. Clinically useful compression often requires more than 15% axial compression, and if a device were available which permitted satisfactory axial compression of the order of 25% of its length, additional clinical benefits would accrue.

Thus, while compression of the order of 15% is of benefit in compensating for errors in measurement of length or the position of the actual implant, a more compressible implant also provides the opportunity of universal fitting. In this case, an implant which is rather long can be kept in stock for emergency purposes, its length being tailored to fit the patient at the time of implantation just by compressing the implant along its axis until it has the correct length for the patient's anatomy.

An axially compressible graft stent can be constructed by providing graft stents (such as those described previously) wherein the circumferentially-oriented portions of the stent(s) of the graft are significantly longer than the axially-oriented components, wherein the distances between circumferential lengths are smaller than the diameter of the graft so that as the circumferential components are urged toward each other, a controlled fold in the graft fabric develops therebetween without causing excess kinking or invagination into the lumen of the graft. Such stent grafts can also take the form of grafts with stent rings spaced therealong. Graft stents of conventional size operate well when the space between adjacent stent circumferential portions (e.g., rings) lie in the range of 4 mm to 8 mm.

Preferably, there is no rigid attachment between adjacent stent circumferential portions (i.e., they define rings). Most preferably, adjacent rings should be spaced apart by distances measuring between ⅓rd and ⅙th of the diameter of the graft. Preferably, the stent rings should have minimal circumferential length (i.e., planar rings are preferred over rings which are kinked or sinuous as viewed in planes parallel to the graft axis). Successful devices have been made where the stent ring comprises a ring of wire where the wire has a cross-sectional diameter of 0.2 mm to 0.4 mm, although if a loss of strength or larger delivery system can be tolerated, wire cross sections between 0.15 mm and 0.75 mm will provide viable grafts. Other satisfactory devices have been constructed where the stent is formed of an annular tube which has been inflated with a rigidizing polymer. The cross section of the tube preferably lies in the range 1 mm to 6 mm in diameter, and is used to reinforce grafts between 8 mm and 45 mm in diameter.

A structure with similar properties of axial compressibility is provided when the separate stent rings are replaced by a continuous reinforcing strut wound in a helical spiral. In this case, the diameter of the strut preferably lies in the range 0.2 mm to 0.4 mm, although if a loss of strength or larger delivery system can be tolerated, wire cross-sections between 0.15 mm and 0.75 mm will provide viable grafts. The pitch of the helix preferably lies between ⅓rd and ⅙th the diameter of the graft, and practical devices operate well when the pitch lies in the range 4 mm to 8 mm.

It is also advantageous to have some parts of the graft designed to resist axial compression, such as those zones intended to seal against the wall of the native vessel into which the graft has been implanted. Resistance to axial compression can be achieved by a number of means, such as reducing the spacing between adjacent stent rings along the axis of the graft over the region to be stiffened (or reducing the pitch of the helical reinforcement wire), or by using stents which cover a longer section of the graft. Preferably, wire rings or helices are used with close spacing because this yields a relatively incompressible zone on the graft while providing a zone which is more conformable than that provided by a large 'Z' stent.

Typically, the graft material is formed from a woven polyester fabric but the use of PTFE, ePTFE, polyester, polyethylene, polyurethane and other biocompatible polymeric films or fibers are known to or are expected to yield viable grafts.

A number of methods of attaching stent rings/helices can be used, including sewing the ring to the graft, threading the ring through the graft, forming pockets in the graft through which the ring is introduced so that the rings are sandwiched between two layers of the graft, and welding or bonding the ring to the surface of the graft.

The aforementioned grafts are preferably used in conjunction with a delivery system which will retain a graft in a first compacted (radially compressed) state, move the compacted graft to the desired deployment site, and then release the graft at the deployment site so that it can adopt an expanded state. The compacted state can be achieved with the use of an outer deployment sheath which retains the graft in a compacted state. Some form of releasable attachment means (e.g., a wire, cord, rod, tube, or other elongated member) at the proximal and/or distal ends of the graft, and preferably at both ends of the graft, can then be used for positioning and release of the graft.

Figure 26:
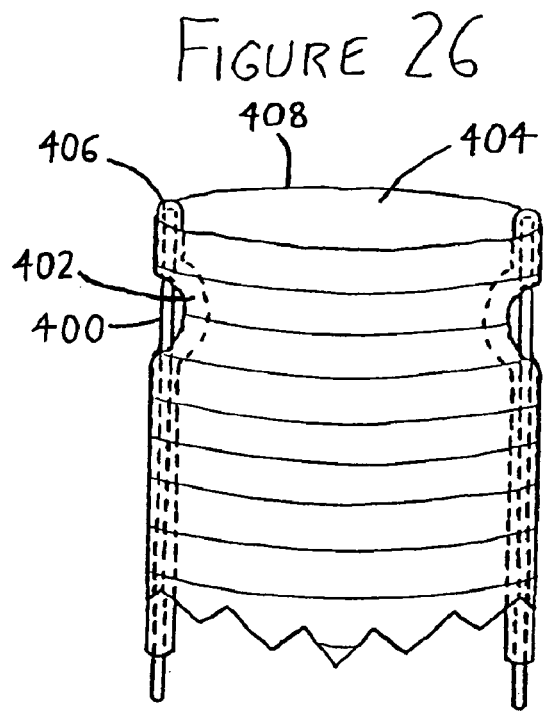
FIG. 26 is a perspective view of a portion of a graft 404 with a means for releasably attaching to the graft 404 to convey it to a desired site, wherein the graft 404 bears a pusher rod inner wire 400 fit within a pusher rod outer tube 402, with the pusher rod inner wire 400 piercing the graft 404 and then reentering the graft 404 and the pusher rod outer tube 402 to engage a pocket 406 at the end of the pusher rod outer tube 402.

The attachment means at the proximal end of the graft (i.e. the end furthest away from the handle of the delivery system) is preferably capable of positioning the proximal end of the graft prior to release. This can be implemented with one or more pusher rod assemblies, as exemplified in FIG. 26, wherein a pusher rod inner wire 400 is fit within a pusher rod outer tube 402. The pusher rod outer tube 402 remains within the interior of the graft 404. The pusher rod inner wire 400 extends through the pusher rod outer tube 402, then exits the side of the pusher rod outer tube 402 to pierce the graft 404, and then reenters the graft 404 and the pusher rod outer tube 402 to engage a pocket 406 at the proximal end of the pusher rod outer tube 402. Thus, when both the pusher rod inner wire 400 and pusher rod outer tube 402 are advanced, they will carry the graft 404 with them because the graft 404 is pinned between the pusher rod inner wire 400 and pusher rod outer tube 402, but when the pusher rod inner wire 400 is retracted from the pocket 406 of the pusher rod outer tube 402, the graft 404 will be unpinned (and thus released). The pusher rod inner wire 400, and then the pusher rod outer tube 402, can then be withdrawn from the graft 404 to leave it in place.

Other arrangements for the proximal attachment means are possible as well. As one example, the arrangement of FIG. 26 can be rearranged to fit one or both of the pusher rod inner wire 400 and pusher rod outer tube 402 outside of the graft 404 rather than inside it. As another example, the graft 404 may be formed with pockets at its proximal end 408 and only the pusher rod wire 400 might be used, and the pusher rod wire 400 may extend inside (or outside) the graft 404 to engage these pockets and allow the graft 404 to be pushed, and also allowing the pusher rod wire 400 to be withdrawn to release the graft 404. As yet another alternative, at least one wire 400 or suture could be threaded through part or all of the graft 404 prior to its deployment, and both of its ends can be attached to the delivery system (e.g., on an outer deployment sheath within which the graft 404 is fitted) so that the graft 404 rides on the wires/sutures 400 during deployment. Upon release of one of the ends of the wires or sutures 400, they can be pulled through the graft 404 to leave it free.

The attachment means at the distal end of the graft (i.e. the end nearest to the handle of the delivery system) is preferably also capable of positioning the distal end of the graft prior to release. This can be implemented simply by employing a push rod or tube which is a close fit within the deployment sheath, and which can be advanced to contact the distal end of the graft and push the distal end through the deployment sheath. Other more complex arrangements are possible as well, e.g., arrangements similar to those used for the proximal attachment means.

It is preferred that the proximal and distal attachment means can be operated and released independently of each other, though combined arrangements are possible.

Most preferably, the graft is delivered to a site in a body by delivering the graft proximate to the site, situating one end of the implant in a first desired position at the site, compressing the implant axially, and situating the opposite end of the graft at a second desired position at the site (the first and second desired positions being spaced from each other, and being spaced by a lesser distance than the length of the fully extended graft). To deliver the graft into a patient in order to treat a lesion (for example, an abdominal aortic aneurysm), the following steps can be used.

Figure 27:
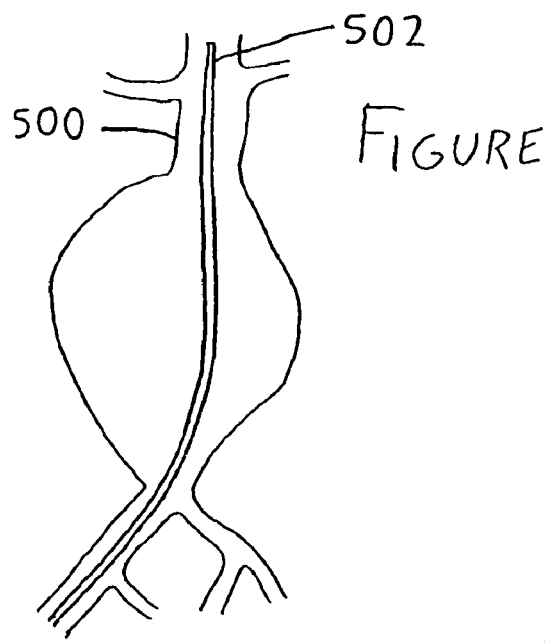
FIG. 27 is a schematic view of a vessel 500 (e.g., an abdominal aortic aneurysm) wherein a guide wire 502 is advanced through the vessel 500 past the aneurysm.

Initially, referring to FIG. 27, a guide wire 502 can be introduced into and advanced through the vessel 500 until it is past the location where the proximal end of the graft is to be fixed.

Figure 28:
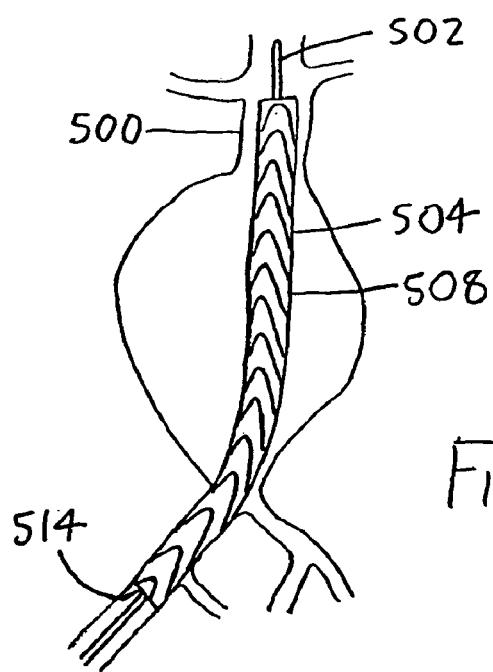
FIG. 28 is a schematic view of the vessel 500 of FIG. 27 wherein an outer deployment sheath 508 is advanced along the guide wire 502, with a graft 512 (shown in subsequent Figures) being situated within the sheath 508.

Looking to FIG. 28, the delivery system 504, with the graft installed therein, can then be advanced along the guide wire 502. The delivery system 504 includes an outer deployment sheath 508, with the graft 512 being within the deployment sheath 508. The deployment sheath 508 is at least substantially inelastic in the axial direction (i.e., it is axially stiff), thereby allowing its advancement to the location where the proximal end of the graft 512 is to be fixed, and its subsequent withdrawal from over the graft 512. The deployment sheath 508 is preferably transparent so that the graft 512 is visible therein, as in the case of FIGS. 28-32.

Figure 29:
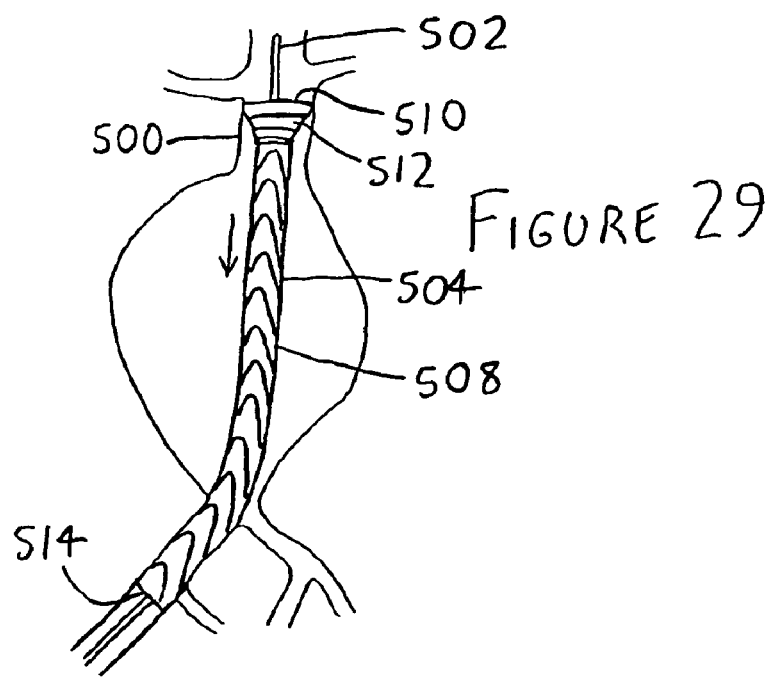
FIG. 29 is a schematic view of the vessel 500 of FIGS. 27-28 wherein the proximal end 510 of the graft 512 is deployed within the vessel by partially withdrawing the deployment sheath 508

In FIG. 29, the proximal end 510 of the graft 512 is deployed, preferably by holding the aforementioned pusher rods 400, not shown in FIG. 29, in place while partially withdrawing the deployment sheath 508 (or alternatively by pushing the pusher rods 400 so that the proximal end 510 of the graft 512 deploys out of the end of the deployment sheath 508, or otherwise actuating the attachment means at the proximal end 510 of the graft 512 so that the proximal end 510 deploys). Note that the graft 512 is generally chosen such that its diameter after deployment will, at least at the proximal end 510, effect an interference fit within the vessel 500 so that it remains fixed in place. However, it could also or alternatively bear spikes, barbs, or other means of grasping the walls of the vessel 500.

Figure 30:
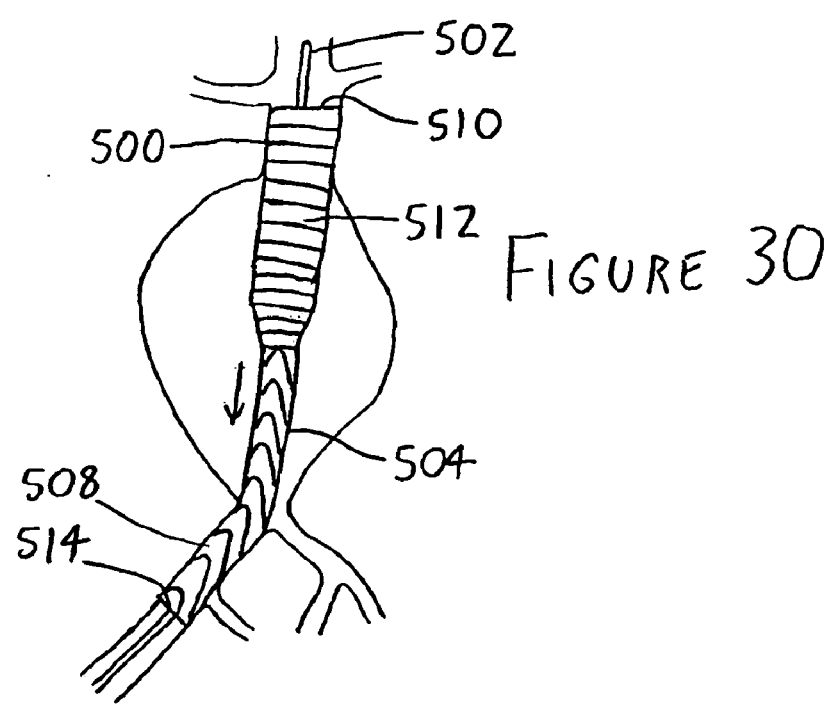
FIG. 30 is a schematic view of the vessel 500 of FIGS. 27-29 wherein approximately half of the deployment sheath 508 has been withdrawn from the graft 512.

In FIG. 30, approximately half of the deployment sheath 508 has been withdrawn. It is preferred that at this time (or slightly before or thereafter), the pusher rods 400 or other proximal attachment means be disengaged from the proximal end 510 of the graft 512. At this point, the proximal end 510 of the graft 512 (and perhaps a portion of its length) should be firmly affixed within the vessel 500, thus alleviating any need for the presence of the proximal attachment means. The proximal end 510 of the graft 512 is therefore now free of the delivery system 504.

Figure 31:
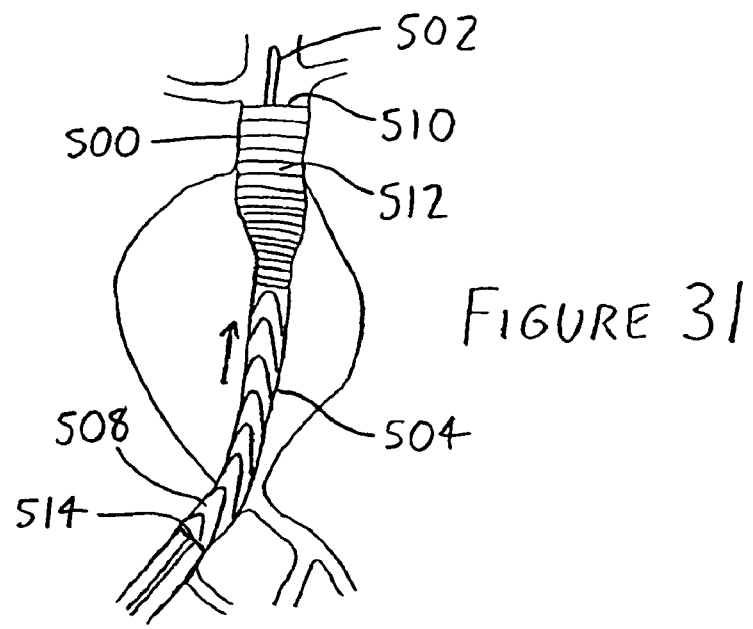
FIG. 31 is a schematic view of the vessel 500 of FIGS. 27-30 wherein the deployment sheath 508 is advanced, compressing the graft 512, to situate the distal end 514 of the graft 512 at its intended distal landing site.

In FIG. 31, the deployment sheath 508 is adjusted to situate the distal end 514 of the graft 512 at the distal landing site. Since a primary benefit of the graft 512 is that it may be chosen longer than needed and may then be compressed to the desired length, the distal end 514 may be pushed toward the proximal end 510- and the graft 512 may be axially compressed—by use of the distal attachment means (e.g., a push rod or tube within the deployment sheath 508). Alternatively, the distal end 514 may be pushed toward the proximal end 510 by moving the deployment sheath 508 in that direction (with the distal attachment means moving therein), and then withdrawing the deployment sheath 508 while the distal attachment means maintain the distal end 514 at the distal landing site. If the distal end 514 is pushed too far towards the proximal end 510, the distal end 514 can be pulled away from the proximal end 510 by means of the deployment sheath 508, which is tightly fit over the graft 512 (i.e., the distal end 514 can be compressed beyond the distal landing site, and then may be extended to reach the distal landing site). Alternatively, if the graft 512 is chosen for an exact fit, the foregoing compression/adjustment need not occur.

Figure 32:
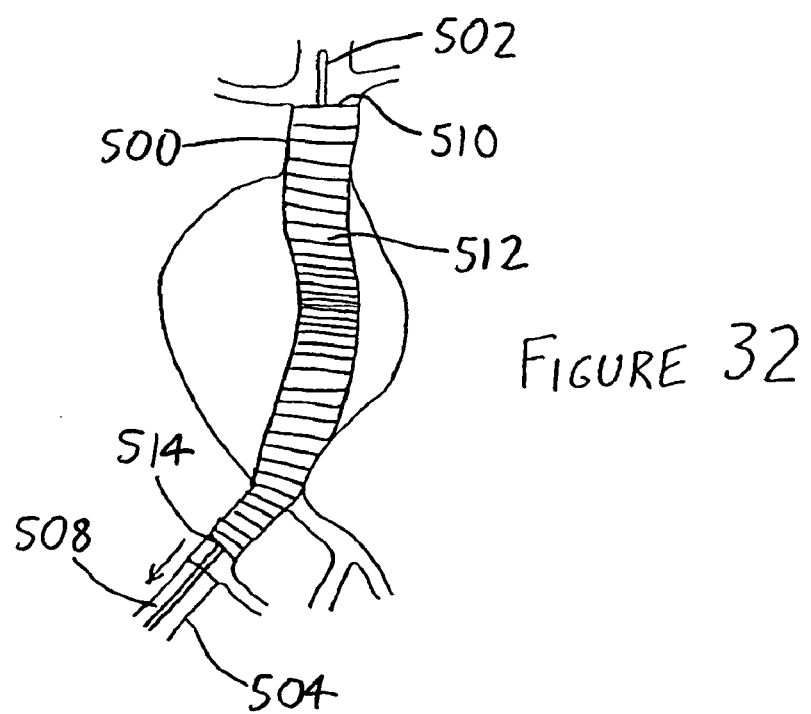
FIG. 32 is a schematic view of the vessel 500 of FIGS. 27-31 wherein the deployment sheath 508 is entirely withdrawn from the graft 512 to leave its distal end 514 at the desired location.

In FIG. 32, the deployment sheath 508 is entirely withdrawn to leave the distal end 514 at the desired location. If necessary, the distal attachment means can be used to situate the distal end 514 at the desired landing site (e.g., the push tube can restrain the distal end 514 at the desired landing site as the deployment sheath 508 is withdrawn). Once the distal end 514 is in place, the distal attachment means, guide wire 502, and any other remaining components of the delivery system 504 may be withdrawn. The distal end 514 preferably remains in place within the vessel 500 via an interference fit, though it may bear spikes, barbs, or other means of grasping the walls of the vessel 500.

If needed, the foregoing steps can be repeated to plug an extension graft component into the deployed component (i.e., another graft branching from a side hole formed in graft 512, a graft to be situated against the graft 512 in end-to-end relation, etc.). In the case of a furcated graft (one wherein one or more branching side grafts extend from the main graft in trunk-and-branch fashion), the foregoing method for positioning the graft may also require that the main or "trunk" graft be properly rotated to align its side holes with vessels that branch from the lumen in which the main or "trunk" graft is situated.

It is understood that preferred versions of the invention have been described above in order to illustrate how to make and use the invention. The invention is not intended to be limited to these versions, but rather is intended to be limited only by the claims set out below. Thus, the invention encompasses all different versions that fall literally or equivalently within the scope of these claims.

What is claimed is:

1. A method of deploying a stent graft between proximal and distal landing sites axially spaced along the lumen of a patient, the method comprising the following steps:
    a. selecting a flexible stent graft having spaced proximal and distal ends, the proximal and distal ends being spaced further apart than the proximal and distal landing sites,
    b. situating the stent graft within a deployment sheath,
    c introducing the proximal end of the stent graft into the lumen of the patient, with the distal end trailing, while the stent graft is within the deployment sheath,
    d. situating:
        (1) the proximal end of the stent graft at the proximal landing site, the proximal end being ejected from the deployment sheath, and
        (2) the distal end of the stent graft away from the distal landing site within the deployment sheath, such that the distal landing site is between the proximal landing site and the distal end of the stent graft; and
    e. subsequently moving the distal end of the stent graft by moving the deployment sheath toward the proximal end until the distal end is situated at the distal landing site, thereby compressing the stent graft along at least a portion of its length, while maintaining the diameter of the stent graft at least substantially unchanged at the compressed portion of the stent graft length, and
    f. ejecting the distal end of the stent graft at the distal landing site.

2. The method of claim 1 wherein the distance between the proximal and distal ends of the stent graft is at least 15% greater than the distance between the proximal and distal landing sites.

3. The method of claim 1 wherein the stent graft is formed of:
    a. flexible sheet material which defines a tubular shape; and
    b. resiliently flexible supports spaced along the axial length of the tubular shape, wherein:
        (1) the supports bias the tubular shape from a radially compacted form to a radially expanded form; and
        (2) the supports are spaced by distances less than one-third of the diameter of the tubular shape.

4. The method of claim 3 wherein the spacing of the supports varies along the axial length of the tubular shape, thereby forming regions of varying axial extensibility of the tubular shape.

5. The method of claim 1 wherein the stent graft is furcated.

6. The method of claim 1:
    a. wherein the stent graft includes:
        (1) an interior axial passage extending between its proximal and distal ends, and
        (2) a side aperture opening onto the interior axial passage between the proximal and distal ends;
    b. further comprising the step of rotating the stent graft to align the side aperture with a lumen branch extending from the patient's lumen.

7. The method of claim 1 wherein:
    the step of situating the proximal end of the stent graft at the proximal landing site includes the substeps of:
        (1) holding the proximal end of the stent graft at the proximal landing site; and
        (2) simultaneously withdrawing the deployment sheath from the proximal end.

8. The method of claim 7 wherein the proximal end of the stent graft is restrained at the proximal landing site by a pushing member extending along the lumen.

9. The method of claim 7 wherein the proximal end of the stent graft is restrained at the proximal landing site by a pushing member which extends through a wall of the stent graft.

10. The method of claim 1 wherein:
    (1) the stent graft may be situated within the deployment sheath with the stent graft being radially compressed, the stent graft radially expanding when released from the deployment sheath;

(2) the stent graft is provided in combination with proximal attachment means for releasably engaging the proximal end of the stent graft, the distal attachment means extending along the deployment sheath;

(3) the stent graft is provided in combination with distal attachment means for releasably engaging the distal end of the stent graft, the distal attachment means extending along the deployment sheath;

wherein:
  a. the proximal end of the stent graft is situated at the proximal landing site by the proximal attachment means; and
  b. the distal end of the stent graft is situated at the distal landing site by the distal attachment means.

11. The method of claim 10 wherein the step of situating the proximal end of the stent graft at the proximal landing site includes withdrawing the deployment sheath from the proximal end of the stent graft while the proximal attachment means maintains the proximal end of the stent graft at the proximal landing site.

12. The method of claim 11 wherein the step of situating the distal end of the stent graft at the distal landing site includes withdrawing the deployment sheath from the distal end of the stent graft while the distal attachment means maintains the distal end of the stent graft at the distal landing site.

13. The method of claim 10 wherein the proximal attachment means includes:
  a. a first elongated member terminating in a pocket, and
  b. a second elongated member adapted to extend alongside the first elongated member, the second elongated member terminating in an end sized to be received within the pocket of the first elongated member.

14. The method of claim 10 wherein:
  a. the stent graft has an at least substantially tubular sidewall extending between its proximal and distal ends; and
  b. at least a portion of the proximal attachment means extends through the sidewall when the proximal end of the stent graft is situated at the proximal landing site.

15. The method of claim 1 wherein the step of moving the distal end of the stent graft toward the proximal end until it is situated at the distal landing site is followed by the steps of:
  a. continuing the motion of the distal end of the stent graft toward the proximal end until it is situated past the distal landing site; and
  b. reversing the motion of the distal end of the stent graft until it is situated at the distal landing site.

16. A method of deploying a stent graft between proximal and distal landing sites axially spaced along the lumen of a patient, wherein the stent graft:
  (1) has spaced proximal and distal ends, the proximal and distal ends being spaced further apart than the proximal and distal landing sites, and
  (2) is axially compressible to allow the proximal and distal ends to be more closely spaced, and wherein the diameter of the stent graft is at least substantially constant during such compression,
the method comprising the following steps:
  a. firstly introducing the proximal end of the stent graft into the lumen of a patient, with the distal end trailing behind, while the stent graft is whithin a deployment sheath;
  b. secondly situating the proximal end of the stent graft at the proximal landing site;
  c. thirdly advancing the distal end of the stent graft by moving the deployment sheath toward the proximal landing site, with the distal end being within the deployment sheath, until the distal end is situated at the distal landing site, with such advancing axially compressing the stent graft; and
  d. fourthly releasing the distal end of the stent graft from the deployment sheath at the distal landing site.

17. A method of deploying a stent graft between proximal and distal landing sites axially spaced along the lumen of a patient, wherein the stent graft:
  I. has spaced proximal and distal ends, the proximal and distal ends being spaced further apart than the proximal and distal landing sites;
  II. is axially compressible to allow the proximal and distal ends to be more closely spaced; and
  III. is provided in combination with:
    i. a deployment sheath wherein the stent graft may be situated with the stent graft being radially compressed, the stent graft radially expanding when released from the deployment sheath;
    ii. proximal attachment means for releasably engaging the proximal end of the stent graft, the proximal attachment means extending along the deployment sheath;
    iii. distal attachment means for releasably engaging the distal end of the stent graft, the distal attachment means extending along the deployment sheath;
the method comprising the following steps:
  a. introducing the deployment sheath into the lumen of a patient with:
    (1) the deployment sheath having the stent graft therein, and
    (2) the proximal end of the stent graft leading the distal end;
  b. locating the deployment sheath within the lumen such that the proximal end of the stent graft is situated at the proximal landing site;
  c. withdrawing the deployment sheath from the proximal end of the stent graft while the proximal attachment means maintains the proximal end of the stent graft at the proximal landing site;
  d. axially compressing at least a portion of the stent graft to move the distal end of the stent graft by moving the deployment sheath toward the proximal end, with the distal end being within the deployment sheath, and with the compressed portion having at least substantially the same diameter before and after compression; and
  e. withdrawing the deployment sheath from the distal end of the stent graft while the distal attachment means maintains the distal end of the stent graft at the distal landing site.

18. The method of claim 17 further comprising the steps of:
  a. moving the distal end of the stent graft toward the proximal landing site to axially compress the length of the stent graft;
  b. continuing such motion until the distal end of the stent graft is situated at the distal landing site; and
  c. releasing the distal end of the stent graft to remain at the distal landing site.

19. The method of claim 17 further comprising the steps of:
  a. after withdrawing the deployment sheath from the proximal end of the stent graft, engaging the distal end of the stent graft with the distal attachment means; and b. moving the distal attachment means toward the proximal landing site to axially compress the length of the stent graft.

20. The method of claim 19 wherein the step of moving the distal attachment means toward the proximal landing site is followed by the step of releasing the distal attachment means from the distal end of the stent graft when the distal end of the stent graft is at the distal landing site.

\* \* \* \* \*